Figure 1:
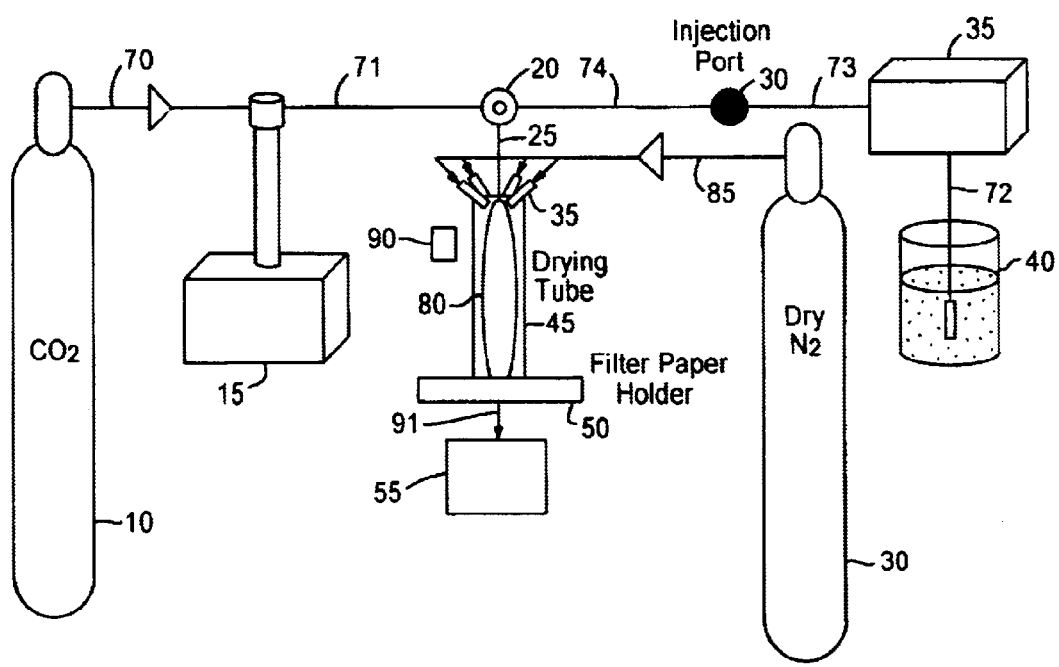

US006630121B1

(12) United States Patent
Sievers et al.

(10) Patent No.: US 6,630,121 B1
(45) Date of Patent: Oct. 7, 2003

(54) SUPERCRITICAL FLUID-ASSISTED NEBULIZATION AND BUBBLE DRYING

(75) Inventors: Robert E. Sievers, Boulder, CO (US); Scott P. Sellers, Burlingame, CA (US); John F. Carpenter, Littleton, CO (US)

(73) Assignee: The Regents of the University of Colorado, Boulder, CO (US)

( * ) Notice: Subject to any disclaimer, the term of this patent is extended or adjusted under 35 U.S.C. 154(b) by 0 days.

(21) Appl. No.: 09/591,213

(22) Filed: Jun. 9, 2000

Related U.S. Application Data
(60) Provisional application No. 60/138,394, filed on Jun. 9, 1999.

(51) Int. Cl.[7] .......................... A61K 51/00; A61K 9/16; A61K 9/50; A61K 9/00; A61B 5/055

(52) U.S. Cl. .................. 424/1.13; 424/9.322; 424/9.35; 424/400; 424/491; 424/497

(58) Field of Search ................................ 516/31; 264/7, 264/12–14; 514/2, 4, 44; 424/1.13, 9.322, 9.35, 400, 491, 497; 128/200.23; 252/305, 314

(56) References Cited

U.S. PATENT DOCUMENTS

| | | | | |
|---|---|---|---|---|
| 4,070,765 | A | 1/1978 | Hovmand et al. | 34/371 |
| 4,582,731 | A | 4/1986 | Smith | 427/421 |
| 4,734,227 | A | 3/1988 | Smith | 264/13 |
| 4,734,451 | A | 3/1988 | Smith | 524/493 |
| 4,845,056 | A | 7/1989 | Yamanis | 501/12 |
| 4,970,093 | A | 11/1990 | Sievers et al. | 427/38 |
| 5,098,893 | A | 3/1992 | Franks et al. | 514/54 |
| 5,100,509 | A | 3/1992 | Pisecky et al. | 159/4.2 |
| 5,266,205 | A | 11/1993 | Fulton et al. | 210/639 |
| 5,301,664 | A | 4/1994 | Sievers et al. | 128/200.23 |
| 5,357,686 | A | 10/1994 | Jensen | 34/169 |
| 5,531,219 | A | 7/1996 | Rosenberg | 128/203 |
| 5,639,441 | A | 6/1997 | Sievers et al. | 424/9.3 |
| 5,639,443 | A | 6/1997 | Schutt et al. | 424/9.52 |
| 5,647,142 | A | 7/1997 | Andersen et al. | 34/373 |
| 5,654,007 | A | 8/1997 | Johnson et al. | 424/489 |
| 5,695,701 | A | 12/1997 | Funder et al. | 264/117 |
| 5,695,741 | A | 12/1997 | Schutt et al. | 424/9.52 |
| 5,707,634 | A | 1/1998 | Schmitt | 424/400 |
| 5,720,938 | A | 2/1998 | Schutt et al. | 424/9.51 |
| 5,725,987 | A | 3/1998 | Combes et al. | 430/137 |
| 5,770,559 | A | 6/1998 | Manning et al. | 514/2 |
| 5,795,594 | A | 8/1998 | York et al. | 424/489 |
| 5,833,891 | A | 11/1998 | Subramaniam et al. | |
| 5,851,453 | A | 12/1998 | Hanna et al. | 264/5 |
| 5,864,923 | A | 2/1999 | Rouanet et al. | 23/295 R |
| 5,922,354 | A | 7/1999 | Johnson et al. | 424/489 |
| 5,928,469 | A | 7/1999 | Franks et al. | 159/48.1 |
| 5,955,108 | A | 9/1999 | Sutton et al. | 424/489 |
| 5,976,574 | A | 11/1999 | Gordon | 424/489 |

(List continued on next page.)

FOREIGN PATENT DOCUMENTS

| | | | |
|---|---|---|---|
| EP | 370 268 | 5/1990 | B29C/33/60 |
| EP | 383569 B1 | 5/1994 | C12N/9/96 |
| EP | 0 667 322 | 8/1995 | C04B/35/00 |
| EP | 706 421 B1 | 12/1998 | B01J/2/04 |
| EP | 767 702 B1 | 12/1998 | B01J/2/04 |
| EP | 0 906 951 A3 | 4/1999 | C12N/1/04 |
| EP | 0 906 951 A2 | 5/1999 | C12N/1/04 |
| EP | 820 415 B1 | 11/1999 | B65D/83/14 |
| EP | 960 951 A2 | 12/1999 | B01F/7/18 |
| EP | 0 711 586 B1 | 8/2000 | B01D/1/18 |
| GB | 2322326 A | 8/1998 | B01J/2/04 |
| GB | 2334900 A | 9/1999 | B01J/2/04 |
| WO | WO 95/01324 | 1/1995 | C07C/215/60 |
| WO | WO 95/03106 | 2/1995 | B01D/15/08 |
| WO | WO 95/21688 | 8/1995 | B01J/2/00 |
| WO | WO 96/00610 | 1/1996 | B01J/2/04 |
| WO | WO 96/32149 | 10/1996 | A61M/11/00 |
| WO | WO 97/41031 | 11/1997 | B65B/1/04 |
| WO | WO 97/41833 | 11/1997 | A61K/9/12 |
| WO | WO 98/17676 | 4/1998 | C07J/31/00 |
| WO | WO 98/29096 | 7/1998 | A61K/9/12 |
| WO | WO 98/29098 | 7/1998 | A61K/9/14 |
| WO | WO 98/29140 | 7/1998 | A61L/9/04 |
| WO | WO 98/29141 | 7/1998 | A61L/9/04 |
| WO | WO 98/36825 | 8/1998 | B01J/2/04 |
| WO | WO 98/58722 | 12/1998 | B01D/11/04 |
| WO | WO 99/16419 | 4/1999 | A61K/9/00 |
| WO | WO 99/16420 | 4/1999 | A61K/9/00 |
| WO | WO 99/16421 | 4/1999 | A61K/9/51 |
| WO | WO 99/16422 | 4/1999 | A61K/9/00 |
| WO | WO 99/19215 | 4/1999 | B65B/1/36 |
| WO | WO 99/44733 | 9/1999 | B01J/2/04 |
| WO | WO 99/59710 | 11/1999 | B01J/2/04 |
| WO | WO 99/66903 | 12/1999 | A61K/9/12 |
| WO | WO 00/00215 | 1/2000 | A61K/39/00 |
| WO | WO 00/10541 | 3/2000 | A61K/9/72 |
| WO | WO 00/15262 | 3/2000 | A61K/47/36 |
| WO | WO 00/61178 | 10/2000 | A61K/38/28 |

OTHER PUBLICATIONS

Edwards, AD. et al., "The Structure and Morphology of Poly(L–Lactide) Particles Formed By Spray Drying and Solution Enhanced Dispersion By Supercritical Fluids (SEDS)" (Apr. 1999) Proceedings of the 18$^{th}$ Pharmaceutical Technology Conference, vol. 1, pp. 37–44.

*Edwards et al., (1998), "Recent advances in pulmonary drug delivery using large, porous inhaled particles," J. Appl. Physiol. 85:379–385.*

(List continued on next page.)

*Primary Examiner*—Ram R. Shukla
*Assistant Examiner*—Jane Zara
(74) *Attorney, Agent, or Firm*—Greenlee, Winner & Sullivan, P.C.

(57) ABSTRACT

A method of making fine dry particles of substances is provided by forming a composition comprising a substance of interest and a supercritical or near critical fluid; rapidly reducing the pressure on said composition, whereby droplets are formed; and passing said droplets through a flow of heated gas. The process does not require any organic solvent.

44 Claims, 21 Drawing Sheets

U.S. PATENT DOCUMENTS

| | | | |
|---|---|---|---|
| 5,985,248 A | 11/1999 | Gordon et al. | 424/46 |
| 5,993,783 A | 11/1999 | Eljamal et al. | 424/46 |
| 5,993,805 A | 11/1999 | Sutton et al. | 424/94.1 |
| 5,994,314 A | 11/1999 | Eljamal et al. | 514/44 |
| 6,001,336 A | 12/1999 | Gordon | 424/46 |
| 6,019,968 A | 2/2000 | Platz et al. | 424/130.1 |
| 6,051,256 A | 4/2000 | Platz et al. | 424/489 |
| 6,054,179 A | 4/2000 | Combes et al. | 427/212 |
| 6,056,791 A | 5/2000 | Weidner et al. | 23/295 R |
| 6,058,624 A | 5/2000 | Bach et al. | 34/374 |
| 6,063,138 A | 5/2000 | Hanna et al. | 23/295 R |
| 6,063,910 A | 5/2000 | Debenedetti et al. | 530/418 |
| 6,068,857 A | 5/2000 | Weitschies et al. | 424/489 |
| 6,071,428 A | 6/2000 | Franks et al. | 252/1 |
| 6,077,543 A | 6/2000 | Gordon et al. | 424/489 |
| 6,080,762 A | 6/2000 | Allen et al. | 514/337 |
| 6,095,134 A | 8/2000 | Sievers et al. | 128/200.14 |
| 6,103,270 A | 8/2000 | Johnson et al. | 424/489 |
| 6,113,948 A | 9/2000 | Heath et al. | 424/499 |
| 6,136,346 A | 10/2000 | Eljamal et al. | 424/488 |
| 6,151,798 A | 11/2000 | Petersen | 34/304 |
| 6,165,463 A | 12/2000 | Platz et al. | 424/130.1 |
| 6,197,836 B1 | 3/2001 | Riede et al. | |
| 2001/0000036 A1 | 3/2001 | Riede et al. | |

OTHER PUBLICATIONS

Hansen et al., (1992), "Supercritical Fluid Transport—Chemical Deposition of Films," Chem. Mater. 4:749–752.

Johnson et al., (1996), "Electrostatic–Enhanced Atomization for Spray Drying of Milk," J. Lebensm.–wiss 4.–Technol. 29:71–81.

Sarbu et al., (May 2000), "Non–fluorous polymers with very high solubility in supercritical $Co_2$ down to low pressures," Nature 405:165–168.

Sato et al., (1984), "The Production of Essentially Uniform–Sized Liquid Droplets in Gaseous or Immiscible Liquid Media Under Applied A.C. Potential," J. Electrostatics 15:237–247.

Sievers et al., (1996), "Supercritical $Co_2$–Assisted Nebulization for the Production and Administration of Drugs," J. Aerosol. Sci. 27:S497–S498.

Sievers et al., (1998), "Supercritical $CO_2$–assisted methods for the production and pulmonary administration of pharmaceutical aerosols," J. Aerosol Sci. 29:S1271–S1272.

Winters et al. (Feb. 1999), "Protein Purification with Vapor–Phase Carbon Dioxide," Biotechnol. Bioeng. 62(3):247–258.

Xu, C.Y. et al., (1998), "Supercritical carbon dioxide assisted aerosolization for this film deposition, fine powder generation, and drug delivery," Green Chemistry: Frontiers in Benign Chemical Synthesis and Processing, Oxford Press, Oxford pp. 312–335.*

Adler, M. and Lee, G. (1999), "Stability and Surface Activity of Lactate Dehydrogenase in Spray–Dried Trehalose," J. Pharm. Sci. 88:199–208.

Allison, D.S. et al. (1998), "Effects of Drying Methods and Additives on Structure and Function of Actin: Mechanisms of Dehydration–Induced Damage and Its Inhibition," Arch. Biochem. Biophys. 358:171–181.

Beach, S. et al. (1999), "Control of the Physical Form of Salmeterol Xinafoate," Org. Proc. Res. Dev. 3:370–376.

Carpenter, J.F. et al., (1998), "Application of Infrared Spectroscopy to Development of Stable Lyophilized Protein Formulations," Eur. J. Pharm. Biopharm. 45:231–238.

Chang, B.S. et al. (1996), "Physical Factors Affecting the Storage Stability of Freeze–Dried Interleukin–1 Receptor Antagonist: Glass Transition and Protein Conformation," Arch. Biochem. Biophys. 331:249–258.

Crowe, J.H. et al. (1998), "The Role of Vitrification in Anhydrobiosis," Annu. Rev. Physiol. 60:73–103.

Dagani, R. (2000), "Better, Cheaper, 'Green ' Solvent," Chem. Eng. News, p. 11.

Dominago, C. et al. (1997), "Precipitation of ultrafine organic crystals from the rapid expansion of supercritical solutions over a capillary and a frit nozzle," J. Supercritical Fluids 10:39–55.

Dong, A. et al., (1990), "Protein secondary structures in water from second–derivative amide I infrared spectra," Biochem. 29:3303–3308.

Dong, A. and Caughey, W.S. (1994), "Infrared methods for study of hemoglobin reactions and structures," Methods Enzymol. 232:139–175.

Dong, A. et al. (1995), "Infrared Spectroscopic Studies of Lyophilization– and Temperature–Induced Protein Aggregation," J. Pharm. Sci. 84:415–424.

Forbes, R.T. et al. (1998), "Production of Stable Protein Particles: A Comparison of Freeze, Spray and Supercritical Drying," presented at the World Congress on Particle Technology 3, Brighton, UK (Jul. 7–9, 1998), 8 pp.

Giessauf, A. and Gamse, T. (2000), "A simple process for increasing the specific activity of porcine pancreatic lipase by supercritical carbon dioxide treatment," J. Mol. Catal. B: Enzymatic 9:57–64.

Hybertson, B.M. (1993), "Pulmonary Drug Delivery of Fine Aerosol Particles from Supercritical Fluids," *J. Aerosol Medicine: Deposition, Clearance and Effects in the Lung,* 6,4:275–285.

Kamihira, M. et al. (1987), "Sterilization of Microorganisms with Superciritcal Carbon Dioxide," Biol. Chem. 51(2):407–412.

Lai, M.C. and Topp, E.M. (1999), "Solid–State Chemical Stability of Proteins and Peptides," J. Pharm. Sci. 88:489–500.

Larson, K. A. and King, M.L. (1986), "Evaluation of Supercritical Fluid Extraction in the Pharmaceutical Industry," Biotechnol. Prog. 2:73–82.

Manning, M.C. et al. (1989), "Stability of ProteinPharmaceuticals," Pharm. Res. 6:903–918.

Meyer, J.D. et al. (1998), "Preparation an in vitro characterization of gentamycin–impregnated biodegradable beads suitable for treatment of osteomyelitis," J. Pharm. Sci. 87:1149–1154.

Mohamed. R.S. et al. (1988), "Solids Formation After the Expansion of Supercritical Mixtures," in *Supercritical Fluid Science and Technology,* Johnston, D.P. et al. (eds.), Am. Inst. of Chem. Eng. Annual Meeting, Washington, DC, Nov. 27–Dec. 2, 1988), pp. 357–378.

Palakodaty, S. and York, P. (1999), "Phase Behavioral Effect on Particle Formation Processes Using Supercritical Fluids," Pharm. Res. 16(7):976–985.

Palakodaty, S. et al. (1988), "Superciritcal fluid processing of materials from aqueous solutions: the application of SEDS to lactose as a model substance," Pharm. Res. 15:1835–1843.

Prestrelski, S.J. et al. (1993), "Dehydration–induced Conformational Transitions in Proteins and Their Inhibition by Stabilizers," Biophys. J. 65:661–671.

Randolph, T.W. et al. (1993), "Sub–micrometer–sized biodegradable particles of poly(L–lactic acid) via the gas antisolvent spray precipitation process," Biotechnol. Prog. 9:429–435.

Reverchon, E. (1999), "Supercritical antisolvent precipitation of micro– and nano–particles," J. Supercritical Fluids 15:1–21.

Reverchon, E. et al. (1995), "Solubility and Micronization of Griseofulvin in Supercritical CHF," Ind. Eng. Chem. Res. 34:4087–4091.

Sarbu, T. et al. (2000), "Non–fluorous polymers with very high solubility in supercritical $CO_2$ down to low pressures," Nature 405:154–168.

Shekunov, B. Yu, Et al. (2000), "Optical Characterisation and Mechanism of Antisolvent Precipitation in Turbulent Flow," Proc. of the $7^{th}$ Meeting on Supercritical Fluids, Particules Design, Materials and Natural Products Processing, Tome 1, Antibes/Juan–Les–Pins, France, Dec. 6,7,8, 2000, pp. 65–70.

Shekunov, B. Yu, Et al. (2000), "Precipitation of Acetaminophen and P–acetoxyacetanilide in Supercritical $CO_2$," Proc. of the $7^{th}$ Meeting on Supercritical Fluids, Particules Design, Materials and Natural Products Processing, Tome 1, Antibes/Juan–Les–Pins, France, Dec. 6,7,8, 2000, pp. 111–116.

Shekunov, B. Yu, et al. (1999), "Crystallization process in turbulent supercritical flows," J. Cryst. Growth, 198/199:1345–1351.

Shishikura, A. et al. (1994), "Separation and Purification of Organic Acids by Gas Antisolvent Crystallization," J. Agric. Food Chem. 42:1993–1997.

Sievers, R.E. et al. (1999), "Formation of Aqueous Small Droplet Aerosols Assisted by Supercritical Carbon Dioxide," Aersol Sci Technol. 30:3–15.

Sloan, R. et al. (1999), "Controlled Particle Formation of Biological Material Using Supercritical Fluids," presented at I.S.A.S.F. $6^{th}$ Meeting on Supercritical Fluids—Chemistry and Materials (Apr. 10–13, 1999), Nottingham, UK (Proc. ISBN 2–905–267–30–5), 6 pp.

St. John, R.J. et al., (1999), "High Pressure Fosters Protein Refolding from Aggregates at High Concentrations," Proc. Natl. Acad. Sci. 96:13029–13033.

Tom, J.W. and Debenedetti, P.G. (1991), "Formation of Bioerodible Polymeric Microspheres and Microparticles by Rapid Expansion of Supercritical Solutions," Biotechnol. Prog. 7:403–411.

Winters, M.A. et al. (1986), "Precipitation of proteins in supercritical carbon dioxide," J. Pharm. Sci. 85:586–594.

York, P. (1999), "Strategies for particle desing using supercritical fluid technologies," PSTT 2(11):430–440.

SUPERCRITICAL FLUID-ASSISTED NEBULIZATION AND BUBBLE DRYING

CROSS-REFERENCE TO RELATED APPLICATIONS

This application takes priority from U.S. provisional application serial No. 60/138,394, filed Jun. 9, 1999, which is incorporated by reference in its entirety herein.

BACKGROUND OF THE INVENTION

With advances in gene therapy and recombinant DNA technology, protein pharmaceuticals are an important class of therapeutic drugs. For example, pulmonary delivery of therapeutic peptides and proteins has received significant attention in recent years, for the treatment of respiratory illness and as an attractive alternative to injection for the systemic delivery of macromolecules. However, the commercial production of protein pharmaceuticals is severely limited by chemical and physical degradation of the proteins which can lead to biological inactivation (Manning, M. C. et al. (1989), "Stability of Protein Pharmaceuticals," Pharm. Res. 6:903–918; Lai, M. C. and Topp, E. M. (1999), "Solid-State Chemical Stability of Proteins and Peptides," J. Pharm. Sci. 88:489–500). Many of these degradation processes use water for hydrolysis and/or other degradation pathways. Therefore, many protein pharmaceuticals are prepared in the solid state as dry powders to prolong the useable shelf life of the product and the storage stability of the product. Protein unfolding in the dried solid can lead to irreversible denaturation upon immediate rehydration and significant reduction of long term storage stability.

Supercritical fluids are substances at a temperature and pressure above a critical temperature and pressure where the substance has a density, compressibility and viscosity intermediate between a gas and a liquid. Near-critical fluids are similar to supercritical fluids and are defined as fluids within 10% of the critical temperature and the critical pressure. For example, since the critical temperature of $CO_2$ is 31.6° C. (304.6K) and the critical pressure is 1073 psi, $CO_2$ above 2° C. (275K) and 966 psi is near-critical. Supercritical fluids have been researched for their use in the production of fine powders of pharmaceuticals, however these technologies (supercritical fluid nucleation (Larson, K. A. and King, M. L. (1986), "Evaluation of Supercritical Fluid Extraction in the Pharmaceutical Industry," Biotechnol. Prog. 2:73–82), rapid expansion of a supercritical solution (Tom, J. W. and Debenedetti, P. G. (1991), "Precipitation of Bioerodible Microspheres and Microparticles by Rapid Expansion of Supercritical Solutions," Biotechnol. Prog. 7:403–41 1) and gas antisolvent techniques (Randolph, T. W. et al. (1993), "Sub-micrometer-sized biodegradable particles of poly(L-lactic acid) via the gas antisolvent spray precipitation process," Biotechnol. Prog. 9:429; Meyer, J. D. et al. (1998), "Preparation and in vitro characterization of gentamycin-impregnated biodegradable beads suitable for treatment of osteomyelitis," J. Pharm. Sci. 87:1149; Winters, M. A. et al. (1996), "Precipitation of proteins in supercritical carbon dioxide," J. Pharm. Sci. 85:586; Palakodaty, S. et al. (1998), "Supercritical fluid processing of materials from aqueous solutions: the application of SEDS to lactose as a model substance," Pharm. Res. 15:1835) require that the pharmaceutical be soluble directly in the supercritical fluid or be precipitated by the supercritical fluid from nonaqueous solvents such as dimethylsulfoxide. The nebulizer system disclosed in U.S. Pat. No. 5,639,441 (Sievers, R. E. and Karst, U., issued Jun. 17, 1997) and divisional application 08/847,310 permits the use of mixtures of supercritical fluids with immiscible liquids such as water to process substances that are not soluble in the supercritical fluid to form aerosols of vapors. Therefore, using the methods and devices disclosed in U.S. Pat. No. 5,639,441 particles of water soluble proteins, excipients, stabilizers, bulking agents and/or surfactants may be formed rather than just particles of those compounds that are soluble in supercritical fluids and/or organic solvents. U.S. Pat. No. 5,639,441 is hereby incorporated by reference, to the extent not inconsistent with the disclosure herein. Unlike the other precipitation methods, e.g., the SEDS process and GAS processes referred to above, no organic solvents are required in the new process; only the drug, water and the supercritical or near-critical fluid (for example, carbon dioxide) are needed.

Even though particles of water soluble proteins and other aqueous formulations can be prepared, no method to form suitable dry powders of these proteins and/or formulations existed until now. Existing technologies to produce dry protein powders, such as spray-drying, freeze-drying, or ultrasonic nebulization, suffer from a variety of problems. In general, dry protein powders are often irrevocably inactivated when produced by prior art methods because the processing steps involved in these methods, temperature required to dry the proteins using these methods and dehydration processes of these methods damage the delicate structure of the protein. Also, for use in direct inhalation applications, powders must be small enough to allow for effective pulmonary delivery. Drug delivery via a pulmonary route is preferred over other delivery routes such as injections for reasons such as decreased pain and delivery of the drug to the desired location more quickly. If the particles produced by the drying process are larger than desired, they must be jet-milled or mechanically ground. This creates an additional physical stress on the molecules and may impart a further loss of protein activity. Dry powders produced in the correct size region could be used directly in dry powder inhalers for pulmonary delivery.

Spray-drying is a currently-available method to produce dry protein powders. In the spray-drying technique, a jet nebulizer is used to form a plume of droplets. In one type of nebulizer, a liquid sample is sucked through a small diameter tube by a high-pressure stream of gas. The gas breaks up the liquid into fine droplets. The gas can also flow across the small diameter tube at right angles and form droplets in a similar manner. Ultrasonic nebulizers use ultrasonic vibrations coupled to the sample solution that cause the solution to break up into small droplets. One disadvantage of the method of spray-drying is the plume of molecules exiting the jet nebulizer is not very dense. This results in a process that is slow in producing a desired amount of protein. Freeze-drying is another currently used method to produce dry protein powders wherein aqueous solutions of drugs are frozen and placed under a vacuum to sublime the water. One disadvantage of the method of freeze-drying is the drying process is very slow. Also, the particles produced are relatively large, requiring additional processing steps to produce pharmaceutically desirable sizes.

U.S. Pat. No. 6,063,138 (Hanna, et al., issued May 16, 2000) and related EP 0767702 describes methods of forming particles of a substance by co-introducing a supercritical fluid; a solution or suspension of the substance in a first vehicle; and a second vehicle which is substantially miscible with the first vehicle and substantially soluble in the supercritical fluid into a particle formation vessel which is maintained at supercritical pressure and temperature.

PCT published application PCT/US99/19306 (WO 010541) (Edwards et al.) describes methods of forming particles by combining a bioactive agent, a phospholipid and an organic solvent or organic-aqueous co-solvent to form a mixture which is then spray-dried.

U.S. Pat. No. 5,695,741 (Schutt et al., issued Dec. 9, 1997) and related U.S. Pat. No. 5,639,443 (Schutt et al., issued Jun. 17, 1997) and U.S. Pat. No. 5,720,938 (Schutt et al., issued Feb. 24, 1998) describe "microbubbles" useful for magnetic resonance imaging and ultrasound imaging. The "microbubbles" are prepared by spray-drying a liquid formulation to produce microspheres having voids and then permeating the microspheres with a fluorocarbon gas osmotic agent.

U.S. Pat. No. 5,928,469 (Franks et al., issued Jul. 27, 1999) describes mixing materials with a carrier substance that is water-soluble or water-swellable and spray drying the resultant mixture to form particles containing both the material and the carrier substance in which the carrier substance is in an amorphous (glassy or rubbery) state. Franks describes spray drying at gas temperatures of 100 to 300° C.

U.S. Pat. No. 6,001,336 (Gordon et al., issued Dec. 14, 1999) describes spray drying suspensions of a hydrophobic component and a hydrophilic component dissolved in an aqueous solution.

U.S. Pat. No. 5,851,453 (Hanna et al., issued Dec. 22, 1998) and related EP 0 706 421 describe a method and an apparatus for forming particulate products by introducing a supercritical fluid and a solution or suspension of a substance in a vehicle soluble in the supercritical fluid into a vessel which is maintained at controlled temperature and pressure. WO 95/01324 (York et al., published Jan. 12, 1995) describes particles of salmeterol xinafoate using this method.

WO 99/16419 (Tarara et al., published Apr. 8, 1999) describes preparing "perforated microstructures" by atomizing a liquid and spray drying the liquid droplets that are formed. WO 00/00215 (Bot et al., published Jan. 6, 2000) describes delivery systems of "perforated microstructures" containing "bioactive agents".

WO 99/59710 (Hanna et al., published Nov. 25, 1999) describes a method and apparatus for forming particles of a substance by dissolving or suspending the substance in a first vehicle which is or contains a first supercritical or near critical fluid and passing that solution or suspension into a particle formation vessel which contains a second supercritical fluid. The vessel is maintained at temperatures and pressures so that the second fluid remains supercritical.

WO 98/36825 (Hanna et al., published Aug. 27, 1998) describes a method and apparatus for forming particles by directing two supercritical fluids, one containing the substance of interest, into a heated and pressurized chamber.

There is a need for stable or pharmaceutically-active proteins in dry form, and a method to produce stable or pharmaceutically-active proteins in dry form. Also, there is a need to produce smaller particles with improved pharmaceutical activities.

BRIEF SUMMARY OF THE INVENTION

This invention provides a method for forming fine dry particles comprising:
(a) forming a composition comprising one or more substances and a supercritical or near critical fluid;
(b) rapidly reducing the pressure on said composition, whereby droplets are formed;
(c) passing said droplets through a flow of gas heated from about 2° C. to about 300° C.

Preferably bubble drying should be conducted at temperatures above ambient temperature and below 100° C. to minimize degradation of the pharmaceuticals. Given sufficient residence time and dilution, a flow of dry gas will dry the fine droplets without external heating. Heating accelerates drying by increasing the vapor pressure of water. The composition may also comprise an aqueous solvent.

Also provided is a method of forming fine dry particles comprising:
(a) mixing an aqueous solution containing the substance of interest and a supercritical or near supercritical fluid, forming a composition;
(b) rapidly reducing the pressure on said composition, whereby droplets are formed;
(c) passing said droplets through a flow of gas heated from about 2° C. to about 300° C.

Also provided is a method of forming fine dry particles comprising:
(a) equilibrating an aqueous solution of the substance of interest with a supercritical or near supercritical fluid, forming a composition;
(b) rapidly reducing the pressure on said composition, whereby droplets are formed;
(c) passing said droplets through a flow of gas heated from about 2° C. to about 300° C.

Also provided is a device for forming fine dry particles, consisting essentially of:
(a) a first pressurized chamber containing a first nongaseous supercritical or near critical fluid;
(b) a second chamber containing a solution or suspension of a substance in a second nongaseous fluid;
(c) a mixing chamber for mixing said solution or suspension and first fluid connected to said first and second chambers by conduits;
(d) first flow control means connected to the conduit between the first chamber and the mixing chamber for passing said first fluid into said mixing chamber;
(e) second flow control means connected to the conduit between the second chamber and the mixing chamber for passing said second fluid into said mixing chamber;
(f) a restrictor connected to said mixing chamber for conducting the composition out of the mixing chamber into a rapid expansion region having a pressure below that of the supercritical or near critical fluid where a dispersion of fine particles of said substance is formed;
(g) a drying chamber connected to the restrictor;
(h) a source of gas connected to the drying chamber at one or more inlets;
(i) means for collecting particles after they pass through the drying chamber.

The mixing chamber is preferably a low dead volume tee.

Fine particles are those with diameter less than about 5 micrometers. Particles formed by the methods of the invention may vary in diameter between about 0.1 micron to about 5 microns. The particles produced may be smaller than 0.1 microns, but current detection methods are size limited in the lower size range, and small particles do not constitute a significant fraction of the mass. The particles may be of any distribution of diameters. For certain applications, for example inhalation therapy, it is preferred that most particles be within the respirable range for delivery to the deep lung alveoli. Preferably the particles range in size from 1 to 3 microns for inhalation applications. Particles may be different sizes for other applications, as known to the art or readily determined without undue experimentation. It is preferred that for inhalation applications, the particles have a small variance from the average size.

As used herein, "dry" or "dried" include particles that include some moisture, preferably not more than 5% by weight Dry particles include those particles which include from 0.0001% to 1% moisture, from 1% to 3% moisture, from 1% to 5% moisture, from 5% to 10% moisture, and combinations of those ranges.

Particles of various shapes are included within the invention. For example, particles may be hollow, or "bubbles". Bubbles are hollow-centered, similar to a tennis ball or a ping pong ball, although they may not be as spherical as a tennis ball or a ping pong ball. The diameter of the particle is typically about 10 to 10,000 times the thickness of the skin. Other particles formed by the method of the invention are not hollow. Higher drying temperatures (~100° C.) favors forming hollow particles, while the same substance may give solid spheres if dried slower at lower temperatures.

"Composition" does not mean all substances are necessarily soluble in each other. Substances which may be made into particles by the methods of the invention include any substance which is either soluble in a supercritical fluid or near critical fluid or mixtures thereof; or a substance which is soluble or suspendable in an aqueous solution. The aqueous solution may also include various co-solvents, but avoiding the use of organic solvents may have environmental and toxicological benefits. Some substances which may be made into particles include: a physiologically active composition comprising one or more substances selected from the group consisting of surfactants, insulin, amino acids, enzymes, analgesics, anti-cancer agents, antimicrobial agents, viruses, antiviral agents, antifungal pharmaceuticals, antibiotics, nucleotides, DNAs, antisense cDNAs, RNAs, peptides, proteins, immune suppressants, thrombolytics, anticoagulants, central nervous system stimulants, decongestants, diuretic vasodilators, antipsychotics, neurotransmitters, sedatives, hormones, anesthetics, anti-inflammatories, antioxidants, antihistamines, vitamins, minerals and other physiologically active materials known to the art. Particles of monoclonal antibodies and vaccines may be produced. Particles of substances such as sodium chloride may also be produced. Some substances may be pharmaceutically-active. "Pharmaceutically-active protein" indicates that the protein has sufficient activity so as to be pharmaceutically useful. Other substances may not be physiologically or pharmaceutically-active.

Various additives may be used in the methods and particles of the invention. These additives may be added to the substance of interest or any solvent used in the process. Additives may also be added directly to the particles after formation. Additives include stabilizers, excipients, bulking agents and surfactants. The use of stabilizers in protein formulations protects against loss of protein activity upon drying. Stabilizers include, without limitation, sugars and hydrophilic polymers, such as polyethylene glycol, hydroxy ethyl starch, dextran or others. The stabilizer is preferably a sugar or mixture of different sugars. Sugars that can be used include mannitol, sucrose, lactose and trehalose, and other mono-, di-, and oligosaccharides. Addition of one or more stabilizers to the protein solution prior to dehydration significantly inhibits the conformational changes within the protein that are believed to be linked to a loss of enzymatic activity. One or more surfactants can be added to alleviate stresses between droplet/air interfaces and decrease degradation that may occur upon drying. Surfactants may be added to alleviate agglomeration or clumping that may occur upon drying. Surfactants are also thought to assist in the formation of spherical particles. Examples of surfactants that may be used include: polyoxyethylene (20) sorbitan surfactants (Tweens), such as Tween 20, Tween 40, Tween 80 and Tween 85; stearic acid; myrj (PEG monostearates), Span 85 (sorbitan trioleate) and polyether-carbonate block copolymers of the type reported in Beckman et al. (2000) Nature 405:165. Phospholipids, including phosophoglyceride may be used. Surfactants and other agents, such as guanidinehydrochloride, may facilitate protein refolding, coupled with pressure treatment. (St. John, R. J. et al. (1999) Proc. Natl. Acad. Sci. 96:13029). Bulking agents and excipients may be inert or active.

If needed for stability of the final formulation, buffer is preferably added first. If more stability is required, sugar may be added. If still more stability may be added, surfactant may be added. A pH buffering substance is useful to counteract the rapid drop in pH from carbon dioxide dissolution at high pressure to form carbonic acid.

For low potency drugs, the fraction of additives in the powder should be minimized; for high potency drugs, inactive excipients (diluents) sometimes constitute more than 99% of the mass. Additives may be added in any useful amount to the composition. Additives are typically used at a concentration of between about 0.001 to 0.5 wt % of surfactant (preferably between about 0.001 to 0.1 wt %), and between about 0.05 to 25% of stabilizer (preferably, when sugar is used, between about 0.1 to 20%, limited by the solubility limit of sugar) by weight to a solution comprising a protein of interest. These percentages are expressed for the aqueous solution before spraying and drying. The final percentage of sugar in the dried powder can be as high as ~99.9%.

The composition may comprise a substance which is soluble in the supercritical or near critical fluid, such as a lipophilic compound. A mixture of supercritical or near critical fluids may be used. The composition may also comprise an aqueous solution or suspension of the substance and a supercritical or near critical fluid (or fluids). Droplets of substances which are not soluble in the supercritical or near critical fluid, such as hydrophilic substances, are then formed. In one embodiment of this method, an aqueous solution comprising a dissolved or suspended compound is pumped into a low-dead volume tee while a supercritical or near critical fluid is pumped into another leg of the tee. The resulting emulsion or supercritical solution pressurized to a pressure near or above the critical pressure of the supercritical fluid (about 70 to about 100 atmospheres when carbon dioxide is used) is allowed to expand to atmospheric pressure out a flow restrictor, forming fine droplets or bubbles containing the dissolved drug species. This aerosol is directed into a drying chamber where solvent evaporation and particle formation takes place.

A second variant of this method allows aerosols to be formed without a low-dead volume tee. In this method, an aqueous solution of precursors is first allowed to equilibrate with a near critical or supercritical fluid in a static canister or chamber, preferably with stirring or agitation. This composition is then allowed to expand to atmospheric pressure out of a flow restrictor, forming fine droplets. These droplets are directed into a drying chamber where solvent evaporation and particle formation takes place.

The initial concentration of the substance of interest in either the supercritical fluid or the aqueous solvent (or solvent mixture) is limited only by the solubility or saturation point of the substance in the solvent or supercritical fluid. Typical starting concentrations are about 1% to about 25% w/w of total solids in the solution or fluid.

Preferably the supercritical fluid is carbon dioxide because carbon dioxide is endogenous and relatively non-toxic, as well as having a critical pressure and temperature easily obtainable. Other supercritical or near-critical fluids may be used, provided that the critical temperature and pressure are obtainable and useful. Carbon dioxide is currently less expensive than any organic solvent and its use avoids VOC emissions. Carbon dioxide's solubility in water is about 2% at 100 atm at near-ambient temperatures.

A number of fluids suitable for use as supercritical fluids are known to the art, including carbon dioxide, sulphur hexafluoride, chlorofluorocarbons, fluorocarbons, nitrous oxide, xenon, propane, n-pentane, ethanol, nitrogen, water, other fluids known to the art, and mixtures thereof. The supercritical fluid is preferably carbon dioxide or mixtures or carbon dioxide with another gas such as fluoroform or ethanol. Carbon dioxide has a critical temperature of 31.3 degrees C. and a critical pressure of 72.9 atmospheres (1072 psi), low chemical reactivity, physiological safety, and relatively low cost. Another preferred supercritical fluid is nitrogen.

The gas that contacts the flow of the droplets is preferably inert, and a preferred embodiment is nitrogen gas, but the gas may be chosen so as to react with the molecule of interest in the course of drying. Preferably the flow of gas contacting the flow of the sample forms a sheath surrounding the flow of the sample, but the flow of gas may contact the flow of the sample by other means such as turbulent mixing. Preferably this gas is heated to a temperature sufficient to cause the desired level of particle drying and also not substantially degrade the biological activity of particles. The gas may be heated to between about 2° C. to about 300° C., preferably below 100° C., although depending on the substance being dried and the constituents of the composition, the temperatures may be adjusted. A preferred range of drying temperatures is between about 35° C. to about 100° C.

Preferably the gas is contained in a drying chamber such as a drying tube. The drying tube is as long as necessary to produce particles having the desired level of moisture by the time the particles reach the end. The drying tube is preferably larger than the diameter of the droplet plume formed from the rapid expansion. The drying tube may be heated, but that is not required. Preferably most of the heat required for vaporizing water is provided by heating the drying gas before it enters the drying chamber. Heating the drying tube may assist in preventing condensation on the surfaces of the tube. The drying tube may be heated externally by means of a lamp such as an infrared lamp, or internally by any means known in the art such as a heating wire imbedded in the material making up the tube. The drying tube may be made from any suitable material which can withstand the temperatures to which it is subjected. Examples of material from which the drying tube can be made are stainless steel or borosilicate glass. Any other design of drying chamber may be used if the desired results are obtained. Other apparatuses, for example a microwave oven, may be used in place of the drying tube to perform the same function.

Rapid reduction of the pressure of the composition is typically performed using a flow/pressure restrictor. The restrictor may be a hollow needle of an thermally conductive material such as stainless steel or a ceramic material, or other material which is able to withstand the pressure and temperature placed upon it. The restrictor may alternatively be a fused silica flow restrictor, or a ceramic multi-channel bundle of capillaries such as that discussed in more detail elsewhere. Also, high pressure sintered stainless steel filters may be used to generate aerosols. The length of the restrictor is typically about 2 inches long; however, the length must not be so long as to cause low flow rates or the precipitation of sufficient solid substance in the restrictor to cause clogging. The restrictor may have as large a diameter as desired, as long as the desired size particles are formed and the pumps have sufficient capacity to maintain the pressure. The lower limit of diameter is determined by the viscosity of the solution being passed through the restrictor. If the viscosity is too high, particles are not formed.

The invention also provides a multichannel restrictor. These openings may be spaced approximately the same distance from each other. The structure may have a cylindrical, a hexagonal, or other shape which allows it to be coupled with the other components used. The openings may be any suitable shape, such as round or hexagonal. An embodiment of one such structure has about 900 non-concentric parallel channels in about a 2 mm total diameter. This multichannel restrictor may have a total diameter which provides the desired particle formation. Preferably each channel has an inner diameter between about 40 μm and about 125 μm. Other multichannel structures may be used, and the openings do not need to be a similar size, although it is preferred if the openings are similarly sized.

The exit tip of the restrictor structure may be flat or substantially flat, or may be shaped. One shape that is particularly useful is formed by removing material from the sides of a flat end, to form an elongated point, similar to a pencil. This modification gives a more dispersed stream of droplets emitted over a 180° angle which is useful to assist in preventing agglomeration of particles as they undergo bubble drying. The particular geometry which gives the best results, depending on the results desired, may be discovered by routine experimentation. Any other means available for reducing the pressure on a composition may be used to accelerate drying.

With many openings through which the composition may pass, the flow rate through the system may be increased and the throughput of the system increased. The overall throughput rate is principally controlled by the total inner diameter of the flow restrictor. Various inner diameters of single channel restrictors may also be used, including 75 micron, 100 micron, 170 micron, and 200 to 1000 micron. Another benefit of multi-channel restrictors over single channel ones is that if one channel becomes clogged, the remainder of the channels remain functional.

The method of this invention may be used for processes in which faster drying than currently available is desired. Fast drying may occur because the swelling/bursting processes of the invention gives greater surface area for drying, although applicants do not wish to be bound by this theory.

Various particles including pharmaceutically-active protein compositions in dry form comprising particles of a protein of interest and optionally containing one or more additives selected from the group consisting of excipients, stabilizers, bulking agents and surfactants, wherein the additives are present at a concentration of about 0.001% to about 99.9%, measured by weight of the dry protein, and wherein the particles have diameters of about 0.1 microns to about 10 microns are produced by the method of this invention. Particles may have a variety of bulk densities depending on the particular substances involved and the conditions under which particle formation and drying occur. For example, particles with bulk densities of between about 0.1 and 1.5 $g/cm^3$ may be formed. The bulk density may be less than 1 $g/cm^3$, less than 0.8 $g/cm^3$, less than 0.5 $g/cm^3$, less than 0.4 $g/cm^3$ or other ranges. Particles may have a variety of activities after rehydration. For example, dry particles with at least 90% of the original activity upon rehydration are included in the invention. Particles with 90–95%, 90–100%, 100–120% original activity are also among those included in the invention.

The particles may be stored in any convenient manner after formation and drying, including placing in bags or other storage devices or additional drying during storage over desiccants such as $P_4O_{10}$ can be undertaken.

Figure 2:
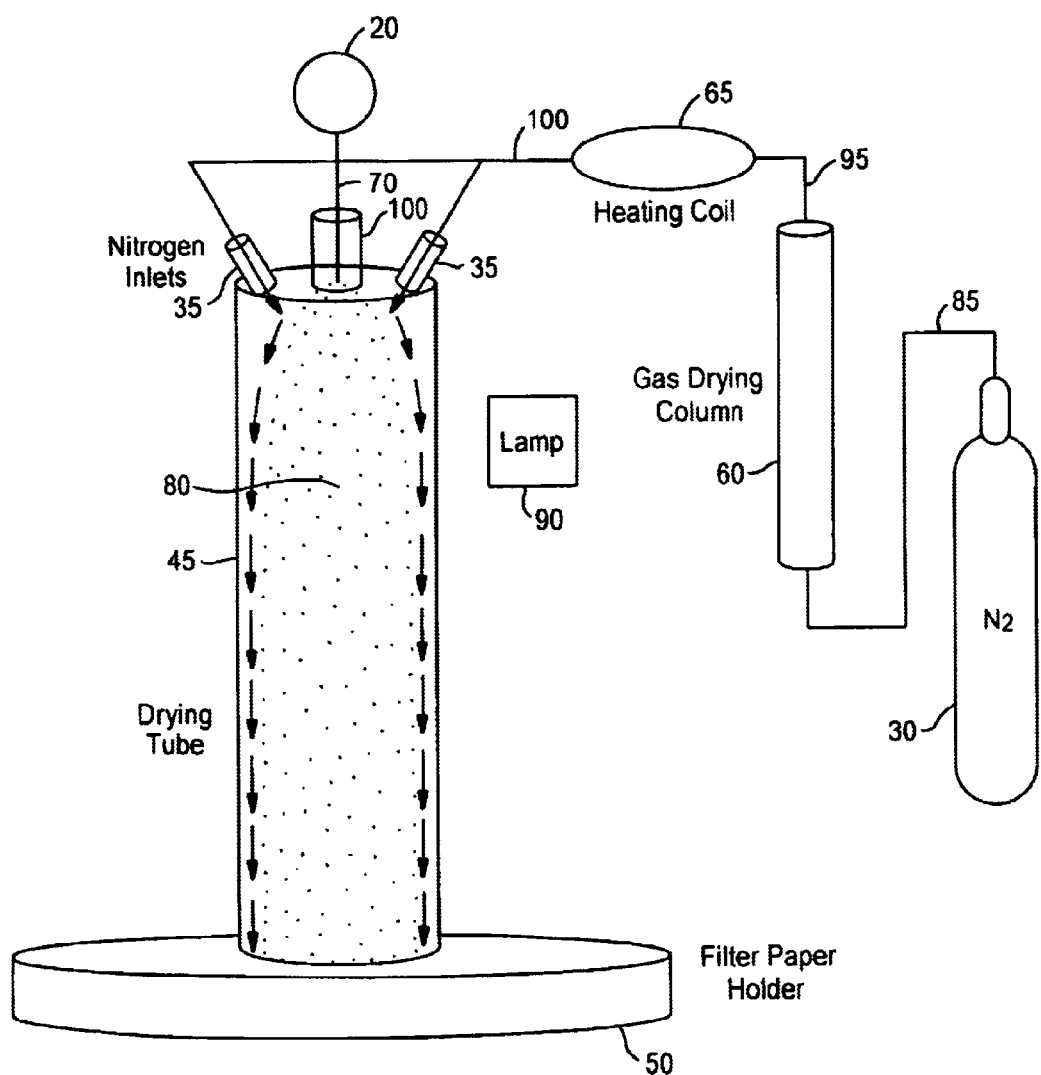

The invention also provides a nebulization system using an injection port that requires a lower volume of sample than currently available systems. This is an advantage when conducting laboratory scale experiments, for example, on costly samples. The injection port also permits equilibration of the nebulization and drying system with the solvents only, followed by introduction of a solution comprising the protein of interest after the system has been equilibrated. This reduces waste of the protein. This nebulization system may be attached to a bubble drying system, or may be coupled with equipment used in conventional spray drying to permit faster drying at lower temperatures.

A method of making droplets by injecting a volume of one or more substances into a flow of a solution comprising an aqueous or supercritical or near supercritical solution using a means for introducing a small sample volume into the flow and subjecting the resulting solution to a rapid pressure decrease to form droplets is provided. Preferably the introducing means is an injection port, such as that used for HPLC. Preferably the volume introduced is about 0.1 mL to about 10 mL.

A method of delivery of proteins or other substances comprising: drying a protein or other substance using the method of this invention, reconstituting the protein with water or other suitable substance, and delivering via desired means is provided.

Stable and/or pharmaceutically active particles are also provided. "Stable" means resistant to decomposition during storage, shipping, reconstitution, and administration.

A device for rapid expansion of a composition comprising a low dead volume tee through which said composition passes and a restrictor with more than one substantially parallel non-concentric channels affixed to said tee is also provided. A low dead volume tee is a mixing tee having a volume of about 0.2 to 10 $\mu$l. The tee may be affixed to the restrictor by any suitable means, for example, epoxy or appropriate fittings.

The drying technique of the invention has advantages over conventional drying techniques. The drying technique of the invention is scalable without significant alteration of particle size or morphology. The method also provides particles having lower density than particles produced by other methods. This leads to particles with small aerodynamic sizes, but large absolute particle dimensions, since in one embodiment, additional gaseous supercritical fluid is formed and leaves the substance of interest containing particles with porous or hollow structures. This permits larger particles with lower momentum to reach the deep lung than would otherwise be possible, in one application.

BRIEF DESCRIPTION OF THE SEVERAL VIEWS OF THE DRAWINGS

FIG. 1 is a schematic diagram of a supercritical fluid assisted nebulization and bubble drying system.

FIG. 2 is a diagram of a drying tube used in the invention.

FIG. 3 is an electron micrograph of the end of a multi-channel flow restrictor.

FIG. 4 is an electron micrograph of a shaped multi-channel flow restrictor.

FIG. 5 is a graph of the buffering capacity of monobasic/dibasic potassium phosphate (♦, pH7), Tris/Tris HCl (▼, pH 7.2), citric acid/sodium citrate (■, pH 5.5), and acetic acid/sodium acetate (●, pH5) upon nebulization with supercritical $CO_2$.

FIGS. 6A–6G are electron micrographs of dry protein powders produced by the method of this invention.

FIG. 7 shows electron micrographs of lysozyme powders produced by the method of this invention with "Buffer only" powder (A) 10% mannitol (B), 10% sucrose (C), and 10% sucrose with 0.01% Tween 20 (D).

FIGS. 8A–B shows X-ray diffraction patterns for samples prepared by supercritical $CO_2$-assisted nebulization of 4 mg/mL lysozyme, 100 mM phosphate buffer at pH 7.0 and 10% mannitol (A) or 10% sucrose (B), with final approximate solid weight percentages in the bubble dried powders of 4% protein, 16% buffer and 80% sugar.

FIGS. 9A–E shows FTIR spectra of lysozyme powders produced by the method of this invention with (A) lysozyme in the native aqueous state; (B) lysozyme containing 10% sucrose and 001% Tween 20; (C) lysozyme with 10% sucrose; (D) lysozyme with 10% mannitol; and (E) lysozyme with buffer only dried at 70° C.

FIG.10 is a graph of the lysozyme enzymatic activity of rehydrated powders, produced using supercritical $CO_2$-assisted nebulization and bubble drying, compared to the activity of the original formulations.

FIG. 11 is a graph of the activity of lactate dehydrogenase (LDH) powders produced by the method of this invention after rehydration.

FIG. 12 is a graph of the recovery of LDH activity using different excipients upon rehydration using different percentages of excipients.

DETAILED DESCRIPTION OF THE INVENTION

The advantages of the present invention over currently used techniques to form dried proteins include the ability to form stable formulations of a variety of different proteins and other materials that are currently unsuitable for drying using presently-available techniques. The present invention imparts lower stress and less severe damage to the substance during drying. Also, the fine powders of stable formulations including proteins formed by this method are prepared directly in the inhalable size region, eliminating the need for additional mechanical micronization which could impart additional stresses to the dried formulation and further loss of activity. The temperatures preferably used in the process of the current invention are much lower than that of conventional drying processes. This decreased temperature of drying results in less extensive thermal degradation. The powders formed by the method of the current invention may retain less water in the prepared powder than with conventional methods, eliminating the need for an additional drying step. The present invention reduces the amount of denaturation and resulting aggregation that is seen with conventional nebulization.

One specifically exemplified embodiment of the present invention is shown in FIG. 1 illustrating the flow of fluids, solutions and particles in the method of this invention. A carbon dioxide reservoir 10 (which can be a gas cylinder or other reservoir) containing liquid carbon dioxide is connected to a carbon dioxide pump 15 (which can be a syringe pump or other suitable pump) via conduit 70. The carbon dioxide pump 15 is connected to mixing tee 20 by means of conduit 71, through which the carbon dioxide is pumped under conditions at which it becomes a supercritical fluid or near critical fluid, when it reaches the heated mixing tee 20. Aqueous solvent reservoir 40 is connected via conduit 72 to fluid pump 35, preferably a high performance liquid chromatography (HPLC) pump, which is connected via conduit 73 to the injection port 30. The injection port 30 is used to add an aqueous solution of protein or other drug, buffer, bulking agent, excipient, stabilizer and/or surfactant. The solution of aqueous solvent from reservoir 40, and protein solution, with or without additives injected through injection port 30, is connected via conduit 74 to mixing tee 20. Mixing tee 20 preferably has a low dead volume, e.g., less than about 10 µl so than an intimate mixture of the supercritical carbon dioxide and the aqueous solution may be formed therein. Mixing tee 20 is equipped with pressure restrictor 25 to maintain back-pressure in mixing tee 20, and may be optionally equipped with heating coils to maintain supercritical temperature therein. Upon passage of the resulting mixture from mixing tee 20 through small diameter pressure restrictor 25, sudden release of the pressure at the exit of the orifice of pressure restrictor 25 occurs and a very fine aerosol of solution droplets and/or bubbles is formed (80). The restrictor may comprise a single outlet, or may consist of many outlets. Aerosol 80 is then directed into the center of drying tube 45. Drying tube 45 is preferably less than 1 meter long and 10 cm in diameter. Nitrogen gas from nitrogen reservoir 30 is added to drying tube 45 via conduit 85 through input ports 35. Preferably a plurality of input ports 35 are arranged equidistant around the center of drying tube 45. Lamp 90 may be used to heat drying tube 45. Nitrogen gas may also be heated as shown in FIG. 2. Heated air or mixtures of gases may be used if there is no explosion hazard. Heat aids in the drying process and keeps water from condensing on the inner walls of the tube and on the filter paper. If the water condenses on the filter paper, it may cause clogging. The output of drying tube 45 is fitted with filter paper holder 50 which is connected to vacuum pump 55 through a suitable connector 91.

In operation, the liquid carbon dioxide is pumped by means of supercritical carbon dioxide pump 15 from carbon dioxide reservoir 10 via conduit 70 through pump 15 and via conduit 71 to the low volume (0.2 to 10 µl) mixing tee 20 where it becomes a supercritical fluid (if it is not already), or a near critical fluid. Pump 35 pumps aqueous solvent from solvent reservoir 40 via conduit 72 where it is pumped via conduit 73 to injection port 30, where the protein of interest is added as an aqueous solution. Additives may also be introduced, either through injection port 30 or to the solvent in reservoir 40. Buffers may be used in the protein solution or aqueous solvent in reservoir 40 to reduce the effect of the possibility of denaturation of the protein and reduce the production of aggregates that may occur due to the otherwise uncompensated pH change due to the introduction of carbon dioxide in the mixture. Mixing tee 20 may be heated by the use of heater coils, and/or restrictor 25 may be heated to maintain the temperature above the critical temperature of the carbon dioxide. The flow of carbon dioxide and aqueous solution are adjusted independently by means of valves, not shown in FIG. 1. Flow rates can also be controlled by altering pumping conditions. The mixture in mixing tee 20 expands downstream and forms aerosol 80 comprising fine particles of the substance dissolved or suspended in the aqueous solution. The particles are directed in the center of drying tube 45 where they are dried and collected on filter paper in filter paper holder 50. Alternatively, particles may be collected using a cyclone separator or cascade impactor, for example, if the particle size distribution is suitable.

The use of injection port 30 allows equilibration of the system prior to introduction of protein and/or additives. Equilibration of the system is reached when the temperature of the drying tube is equilibrated as measured by a thermocouple and the flow rates of aqueous solution and carbon dioxide reach steady states. After equilibration, a known volume of the protein formulation into the aqueous feed line may be injected through injection port 30.

A six-port injection valve may be adapted for use in a nebulization system so that in the load stage, there are two separate solution loops. Solvent is pumped from an HPLC pump through the mixing tee in one loop and the sample is contained within a sample loop, for example a 3 ml sample loop, that is not connected with the solvent loop in the load stage. During the inject stage, solvent is pumped from the HPLC pump through the sample loop and to the mixing tee. This modification has the advantage of not pumping protein or other substances of interest through HPLC pistons and allows the ability to inject very small samples. The amount of protein required per run and the overall run times are substantially decreased.

When a sample injection valve is used, typical system parameters include: carbon dioxide pressure 100 atm; carbon dioxide flow rate 0.3 ml/min; aqueous flow rate 0.3 ml/min, using a 5 cm long fused silica restrictor with 50 µm inner diameter.

FIG. 2 shows a more detailed view of the drying tube and drying process. The solution from mixing tee 20 is passed through restrictor tip 70 into drying tube 45 through inlet 100, where droplets are formed. Nitrogen (or other gas, either inert, or containing a substance that is desired to react with the aerosol particles) from reservoir 30 is passed via conduit 85 to gas drying column 60. The gas is then passed via conduit 95 to heating coil 65. In a preferred embodiment, the gas is heated to around 70° C. and is present at a flow rate of around 15 L/min. Heated gas is passed through conduit 100 to drying tube 45 via gas inlets 35. In a preferred embodiment, drying tube 45 is a glass tube with 5 input ports, one in the center where the aerosol is added, and 4 other inlets arranged around the center port. Lamp 90 is also used to heat drying tube 45 externally. At the output of drying tube 45, the particles are collected on filter paper held in holder 50.

Other configurations of drying tube 45 may be used. For example, more or fewer inlet ports 35 may be used. The gas may also be added to the center of the tube, and the particles added around the gas. Gas and particles may also be mixed together in the drying tube. The interaction of the drying gas and particles in the tube affect the characteristics of the final product.

Preferably all high pressure parts are made from stainless steel. Other inert materials or coatings may be used. Preferably filter paper holder 50 is made from stainless steel. The restrictor length is preferably about 2 in. (5 cm). The flow rates for the aqueous solutions in the above apparatus are about 0.5 ml/min to about 3 ml/min. If desired, the process may be conducted on a larger scale or smaller scale by adjusting dimensions and flow rates while maintaining similar temperatures and pressures. In the specifically exemplified embodiment, flow rates of carbon dioxide and aqueous solvent are approximately 0.3 mL/min. when using a 50 µm inner diameter flow restrictor.

Injection port 30 allows several small volume aliquots (about 0.1 to about 10 ml) of protein formulations to be introduced in the same amount of time as required by one large volume (>10 ml) in a system without the injection port.

This permits several protein formulations with varying components and concentrations to be dried quickly with small amounts of protein used in each run. This is a significant advantage to commercial laboratory scale spray driers which require up to 100 ml of protein solution per experiment. However, the method of the invention may also be practiced with larger volumes of proteins and with larger volumes of any substance desiring to be dried.

Figure 3:
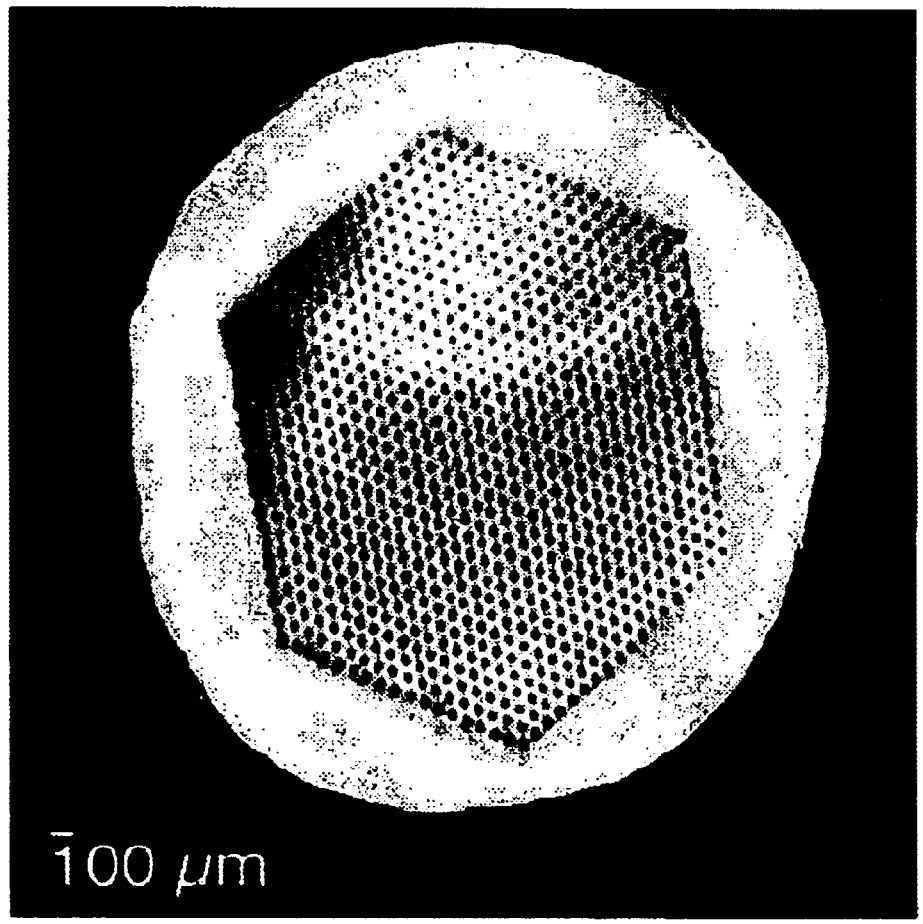

The restrictor may be a multichannel restrictor having a plurality of parallel tubes. One such multichannel restrictor may be fabricated from a glass multi-channel column (Alltech, Inc., Illinois). This column may be purchased in lengths up to 1 meter with about 900 holes through the length of the column each hole having an inner diameter approximately 40 or 50 microns or greater. A piece of such column can be used as a multichannel restrictor. One such product has a hexagonal shape (Alltech part number 17059). Other products have a round shape where the hexagon is placed in a circle of the same diameter. An electron micrograph of the end of such a restrictor is shown in FIG. 3. The round shape restrictors are easier to attach to pumps and canisters with ferrule seals and Swagelok fittings and they can also be attached to stainless steel tubing or tee by applying epoxy pre-polymer mixture to the exterior of the glass or ceramic tubing and slipping it into a slightly larger steel tubing. The hexagonal voids can be filled with polymers or epoxys. These multichannel restrictors may be used in both static or dynamic processes. In a dynamic process, a low dead volume tee is used to intimately mix streams of liquid (near critical ) or supercritical fluid such as carbon dioxide with an aqueous solution or suspension to be nebulized. In the static process, a solution of a substance of interest is pressurized by supercritical or near critical fluid at a temperature near its critical temperature. This allows some of the supercritical or near critical fluid (up to about 1 to 2 mole percent if carbon dioxide is used) to be dissolved in the water. When the solution approaches equilibrium, with mixing, if the aqueous solution and supercritical or near critical fluid are allowed to be ejected through a pressure restrictor, an aerosol is formed as the fluid exiting the pressurized fluid returns to atmospheric pressure or lower. The multichannel restrictor can also be used in the gas antisolvent methods, and any other methods where particles are desired.

Figure 4:
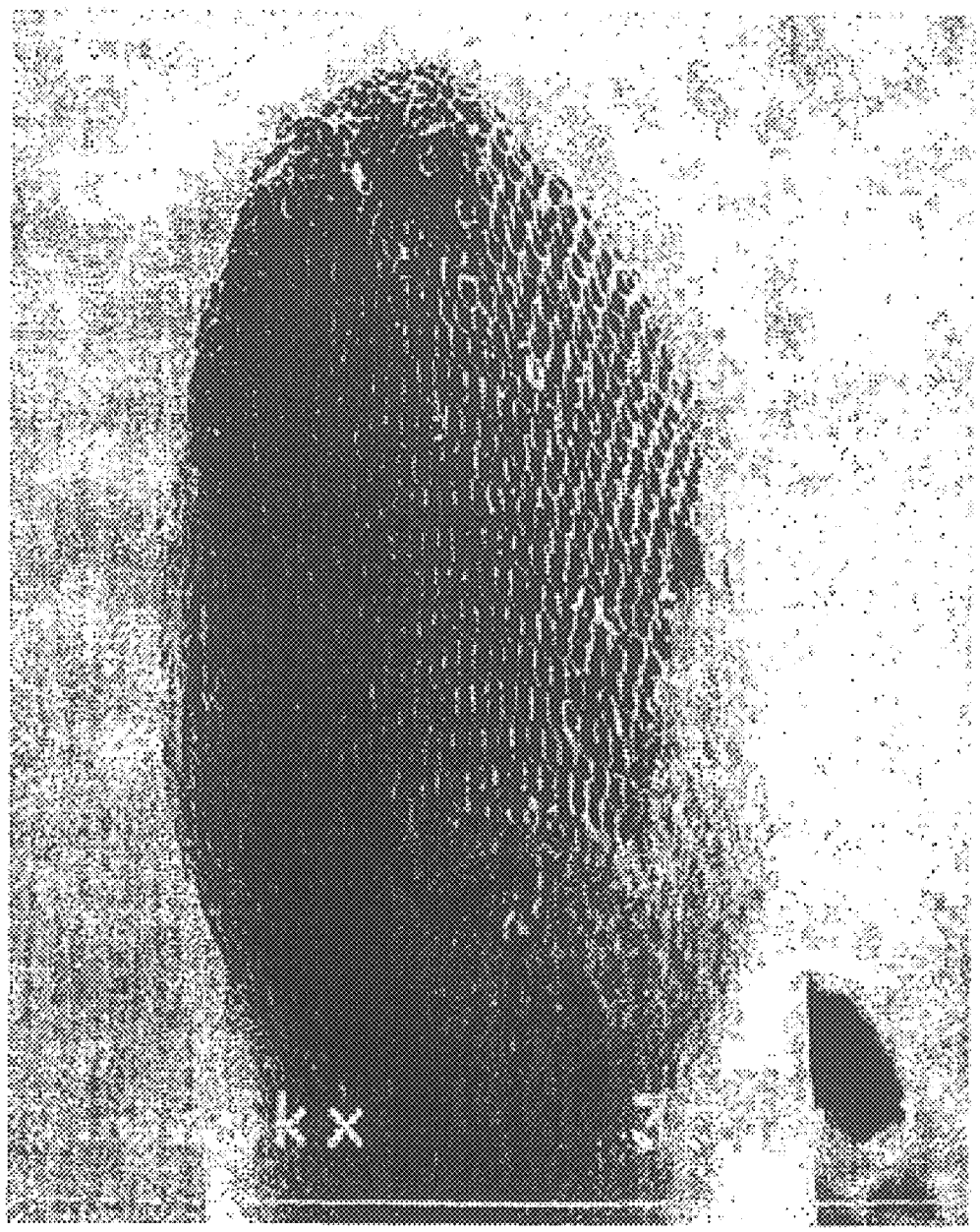
Figure 5:
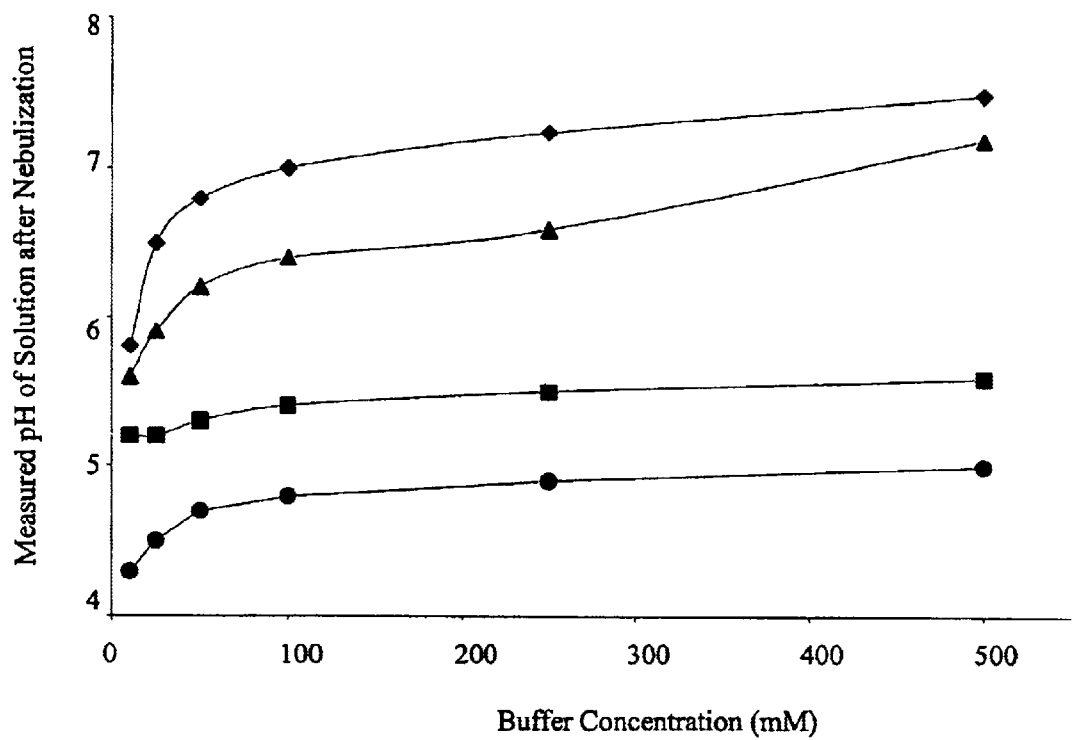
Figure 6A:
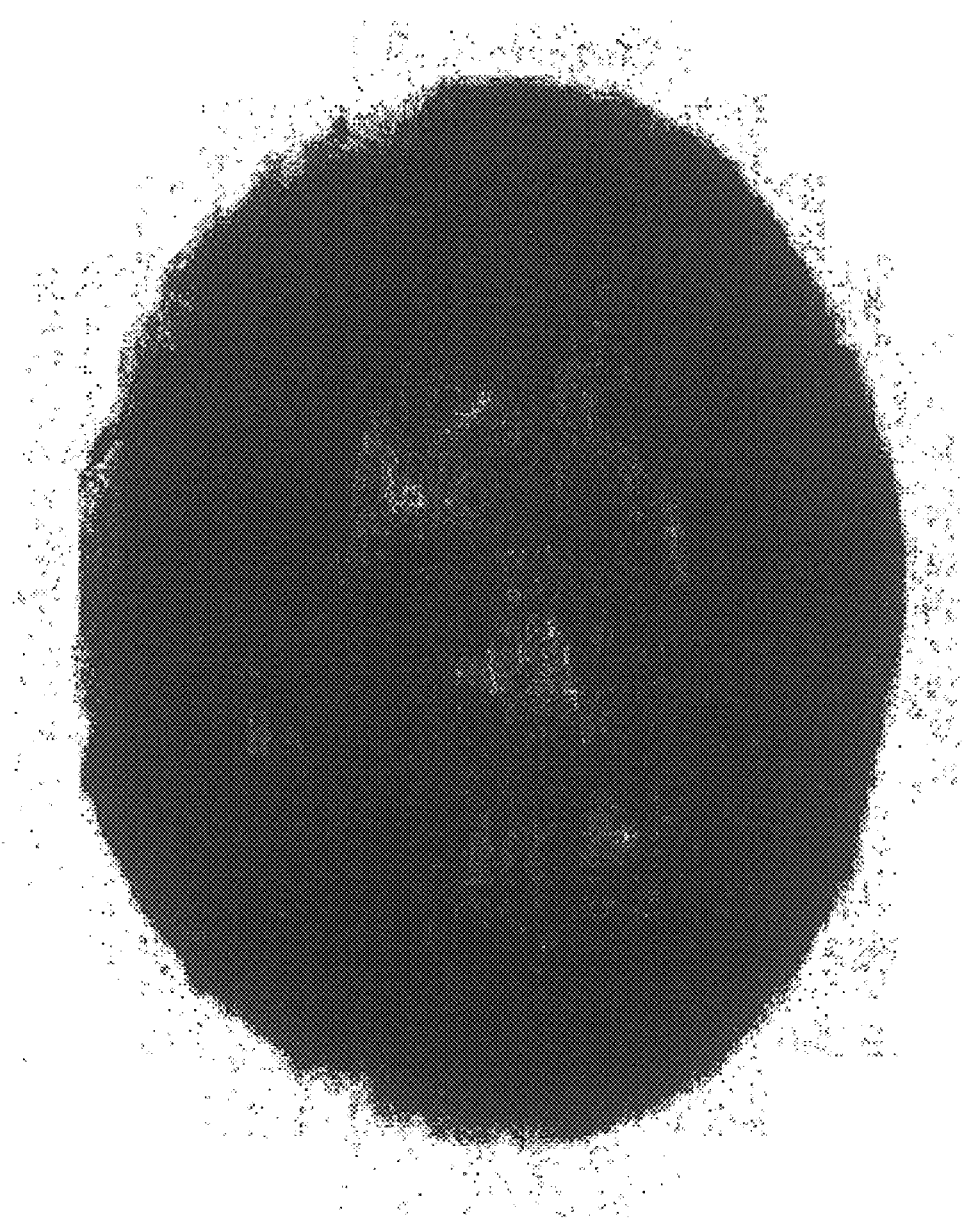
Figure 6B:
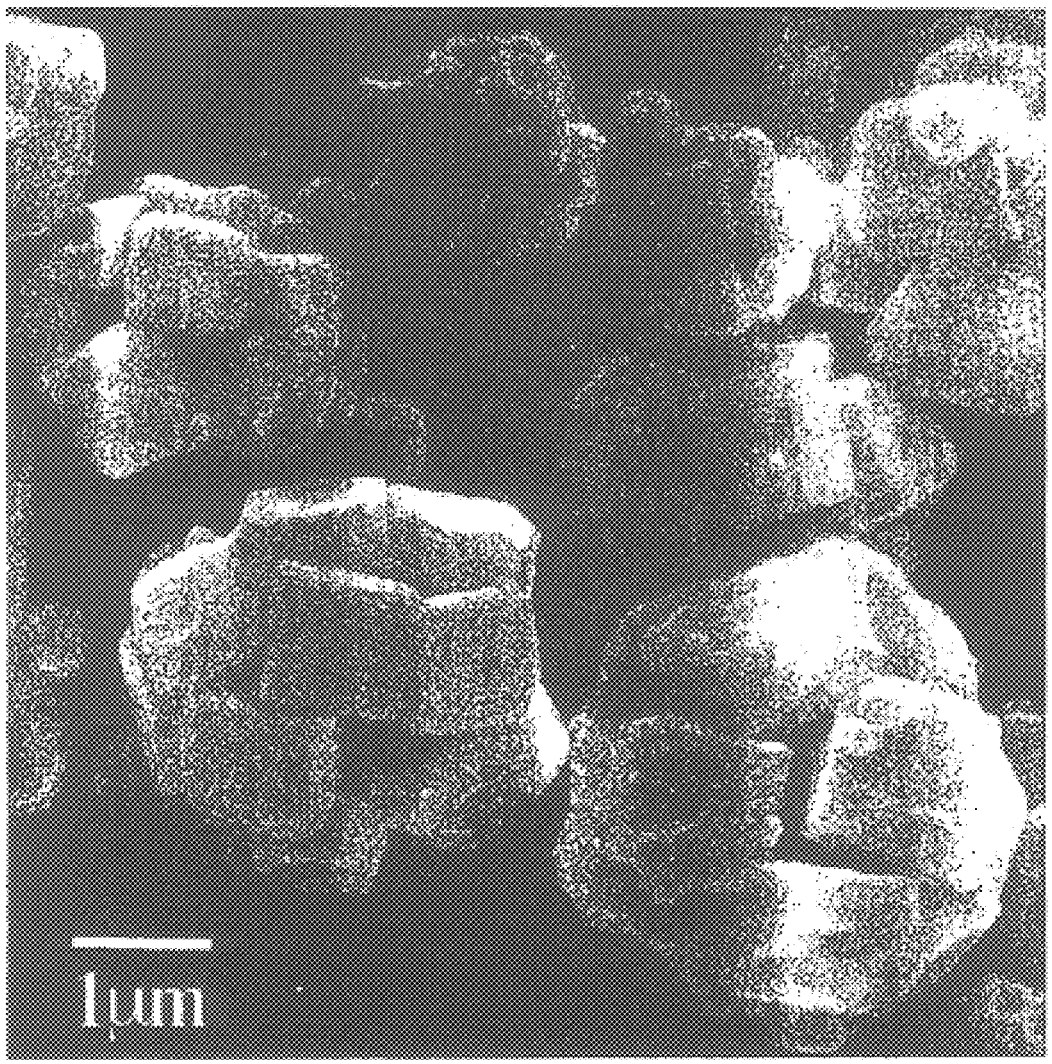
Figure 6C:
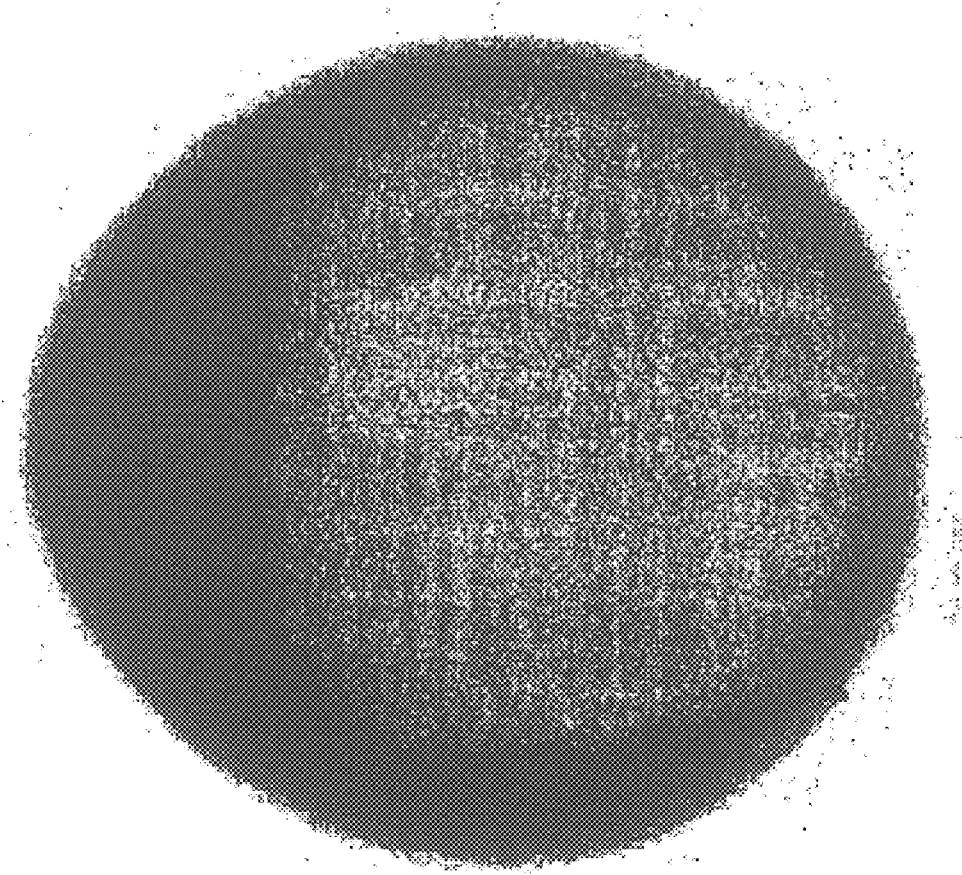
Figure 6D:
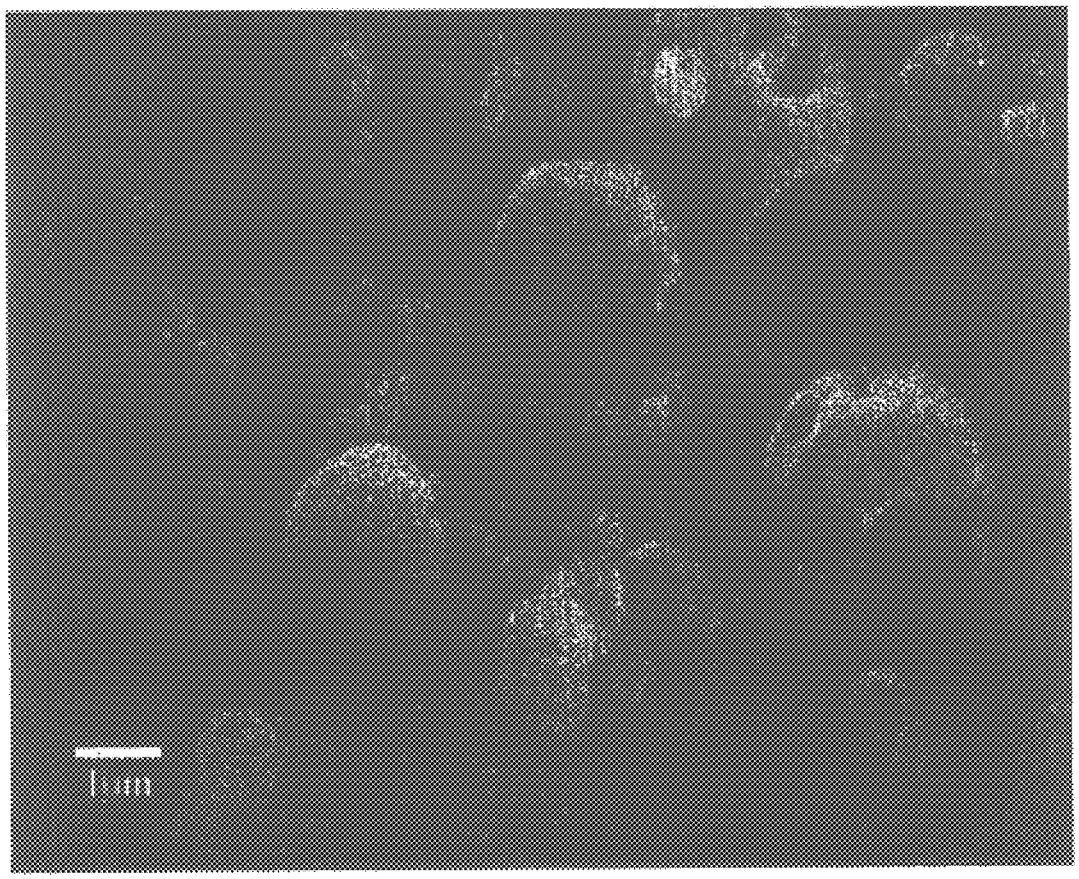
Figure 6E:
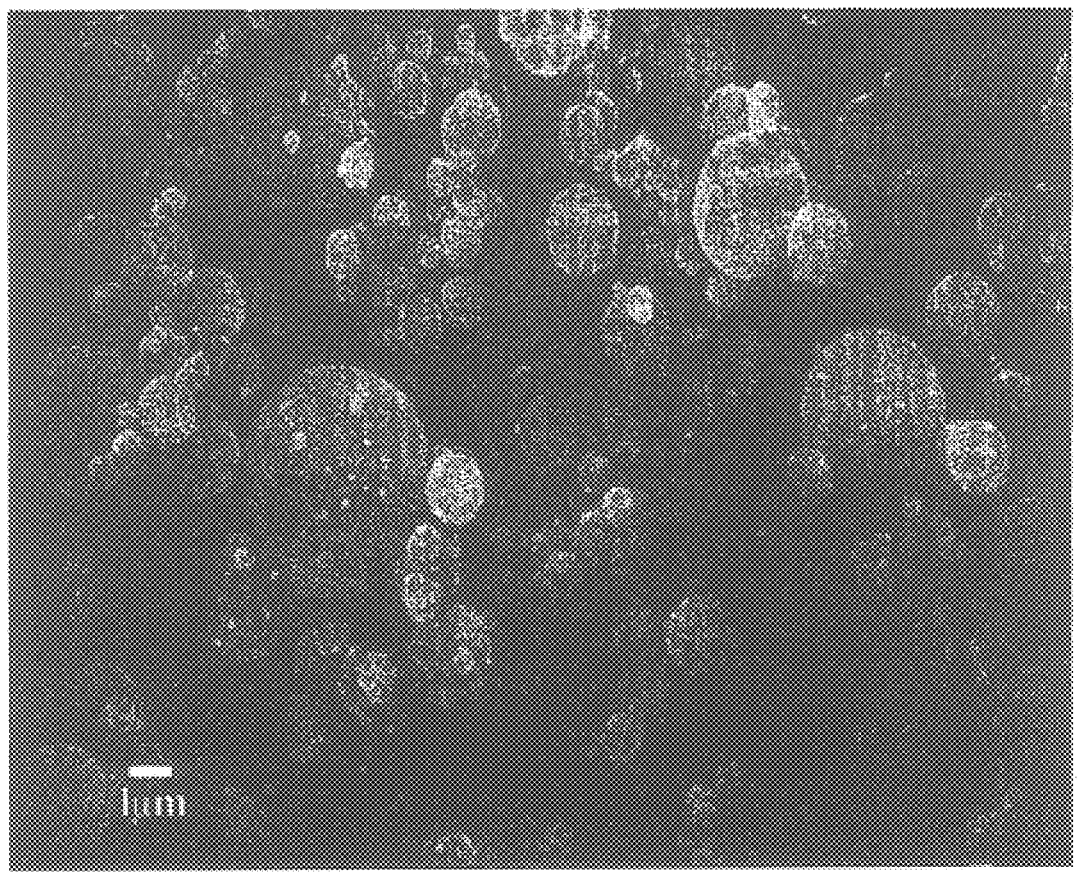
Figure 6F:
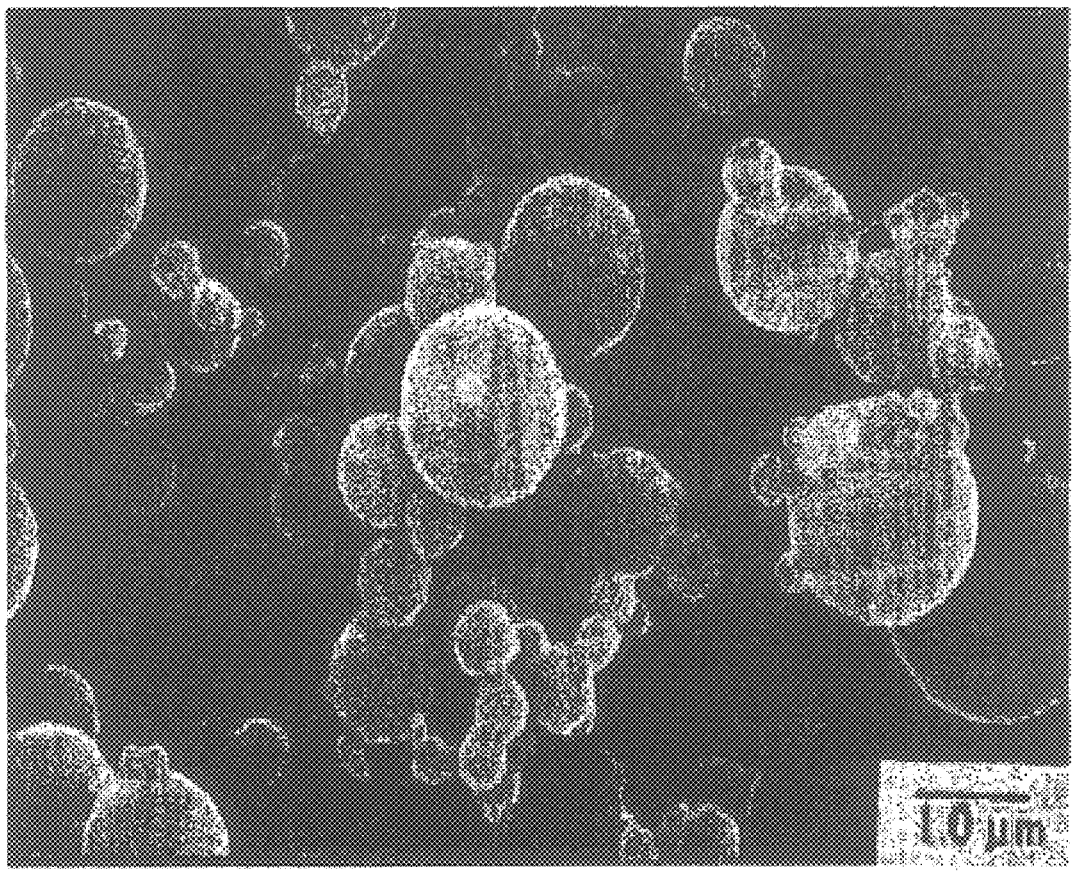
Figure 6G:
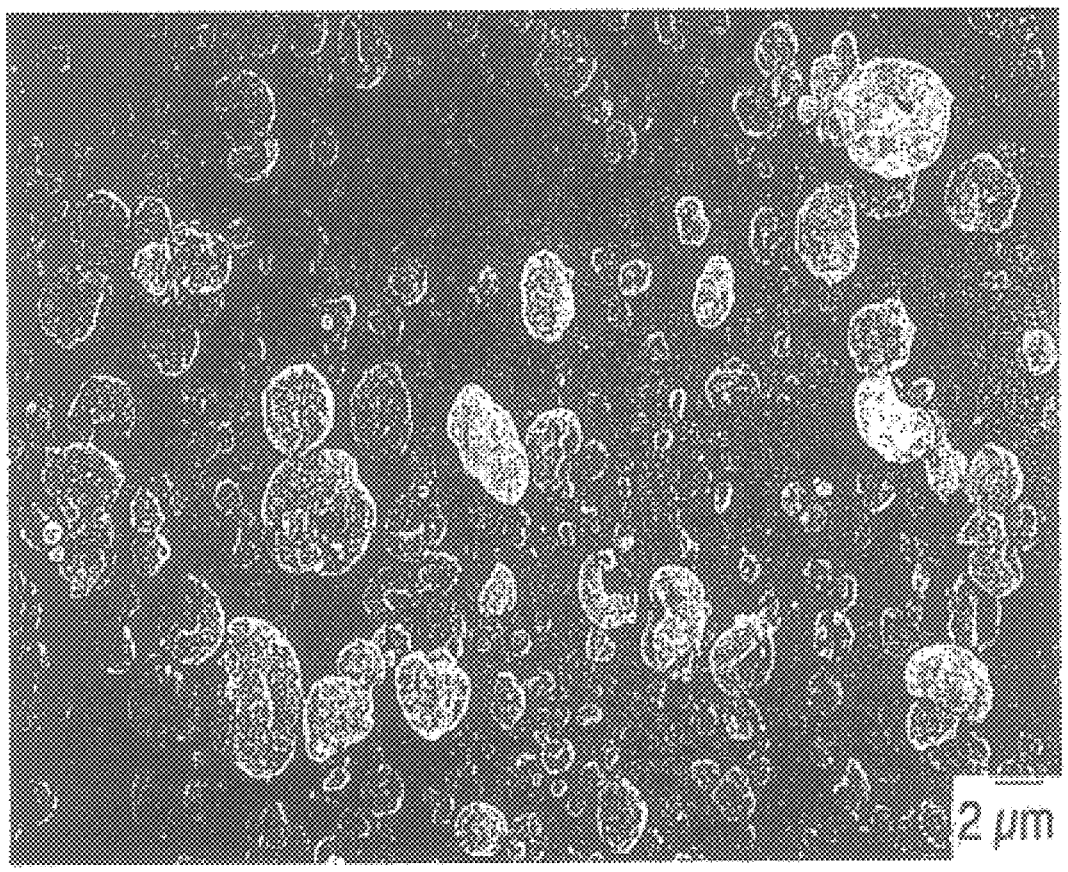
Figure 7A:
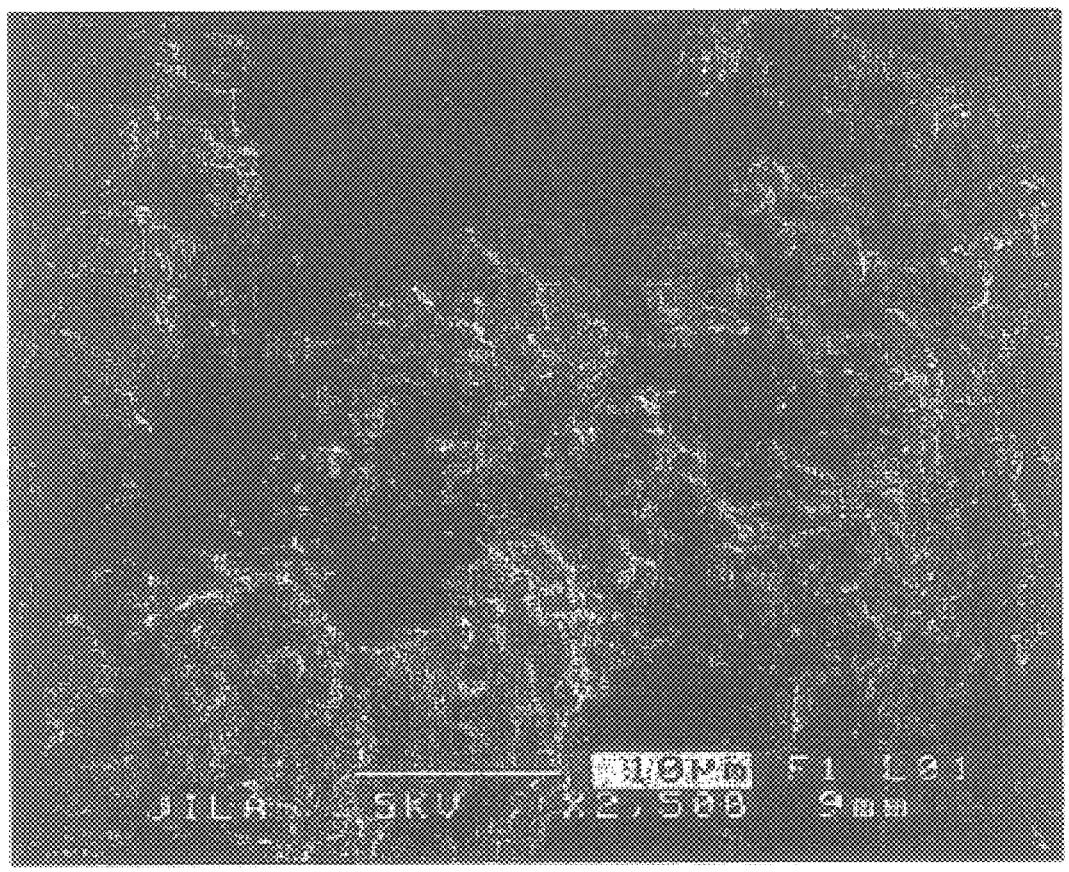
Figure 7B:
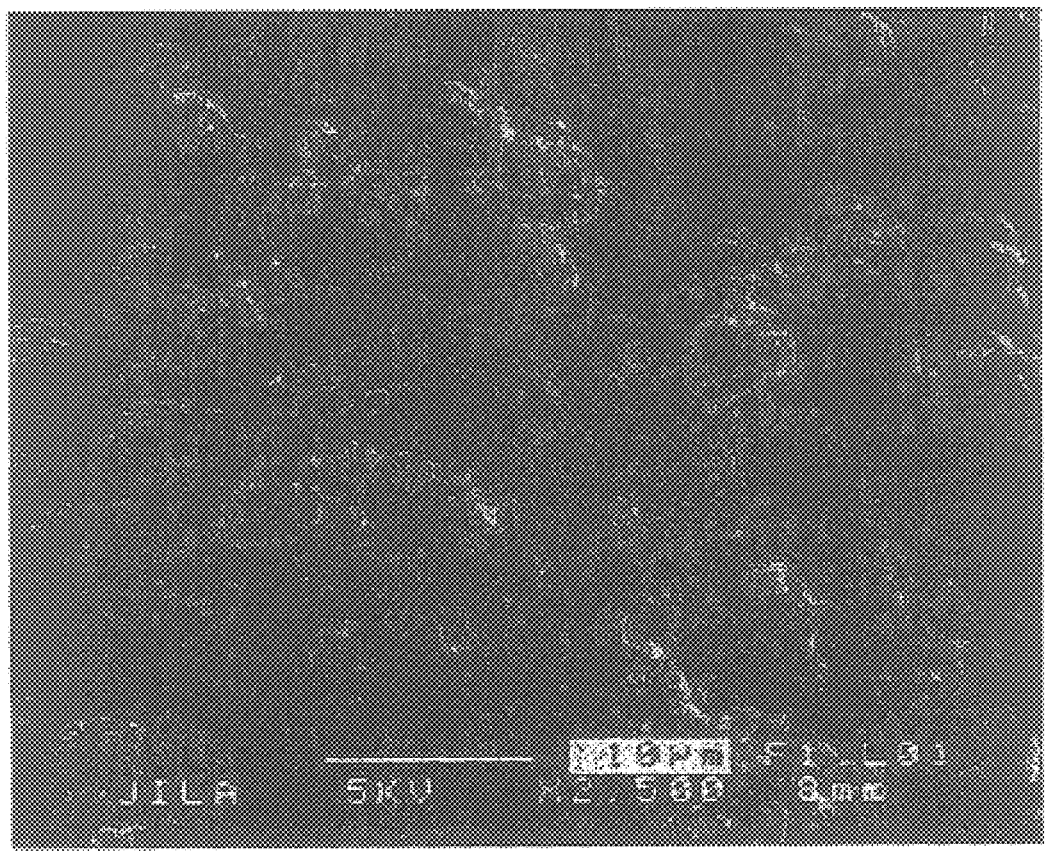
Figure 7C:
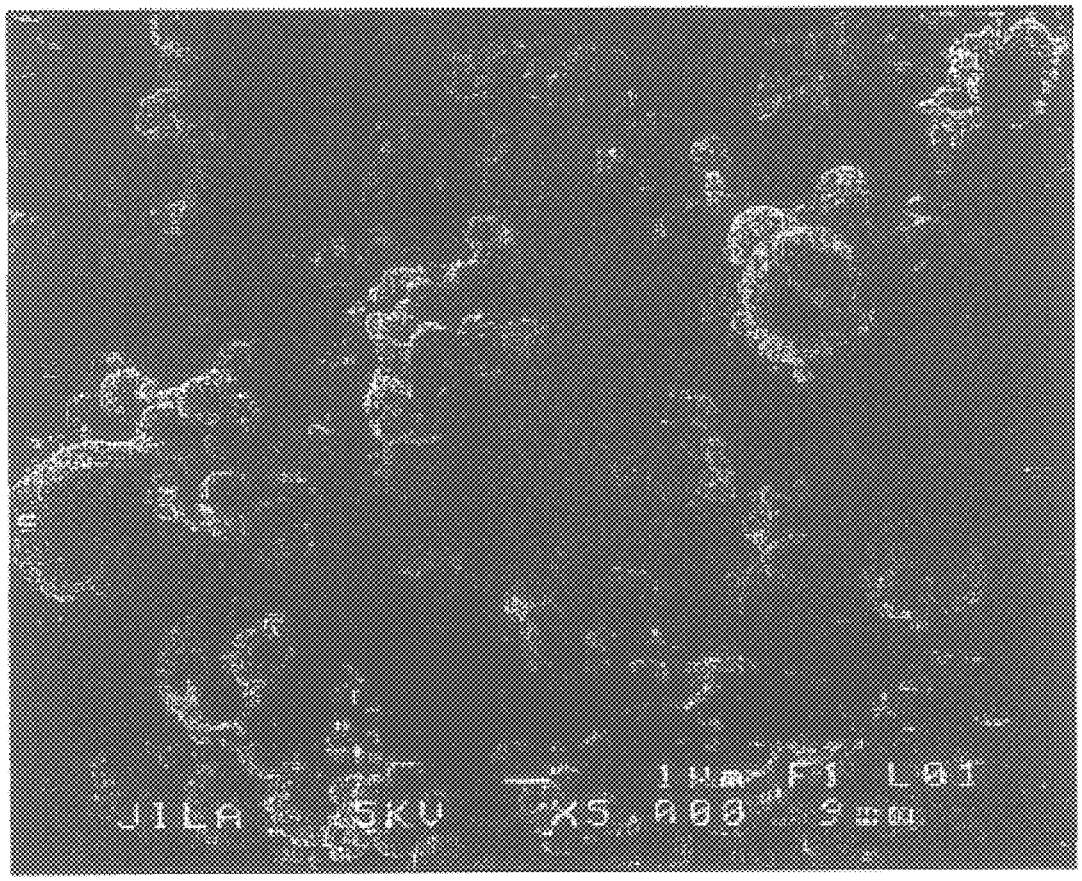
Figure 7D:
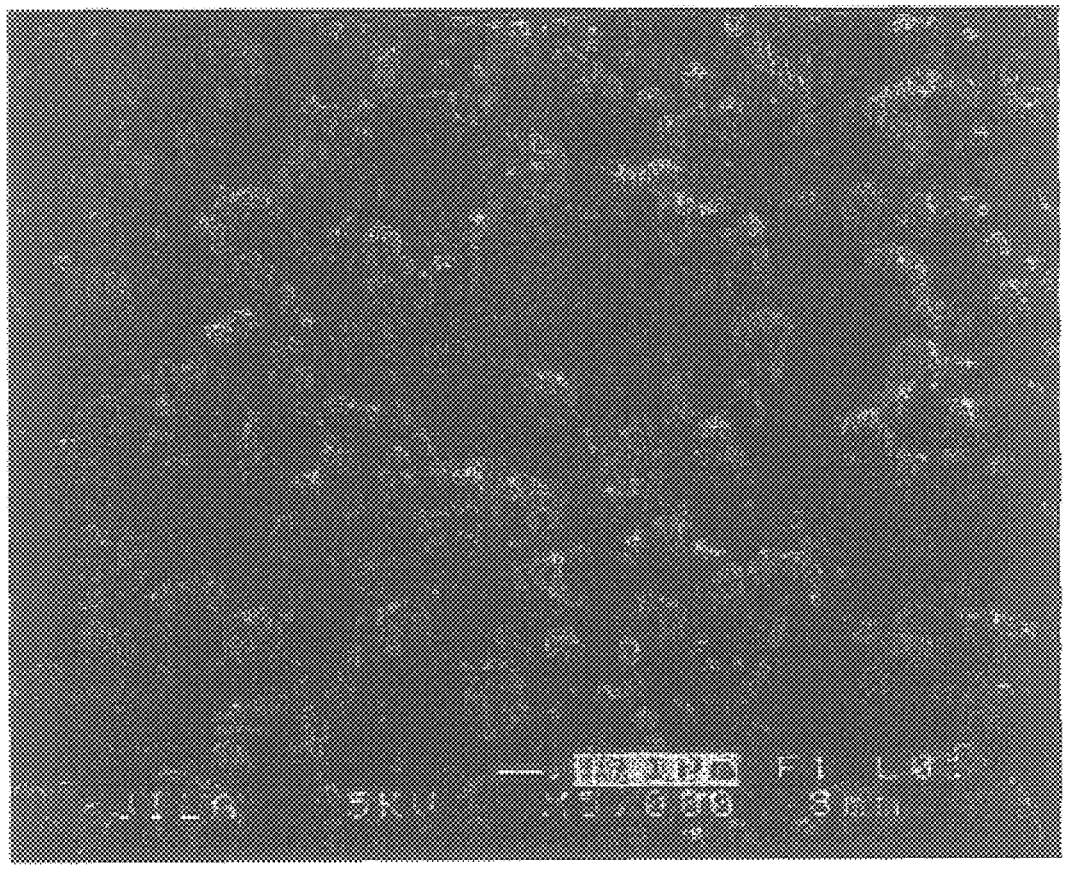
Figure 8:
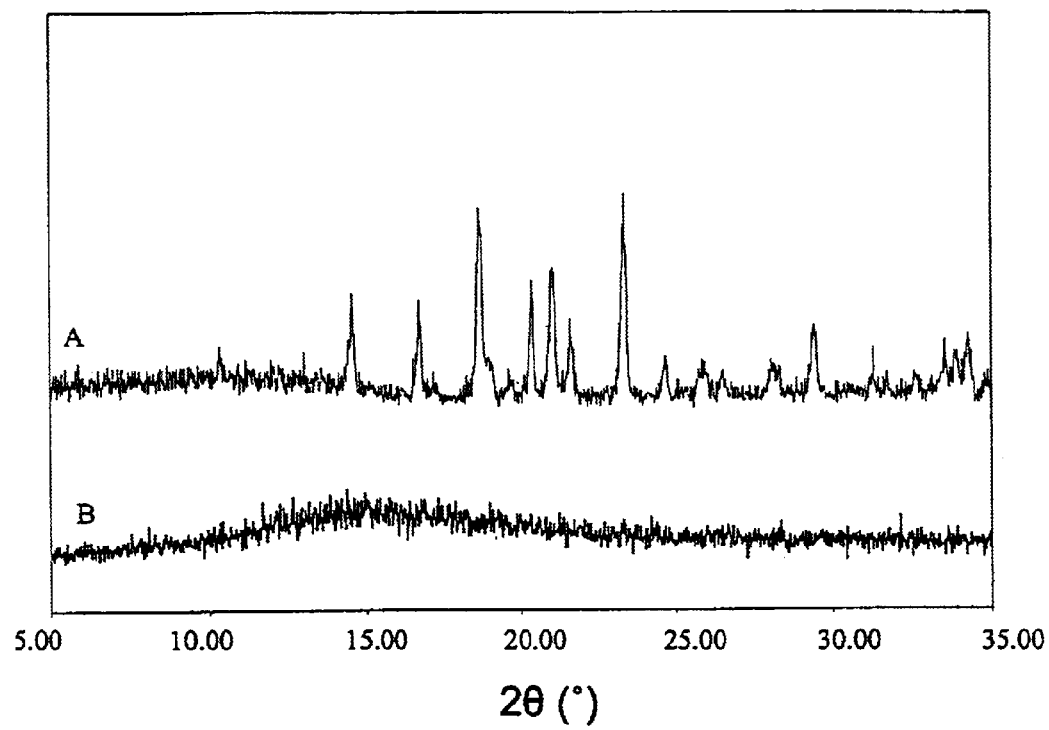
Figure 9:
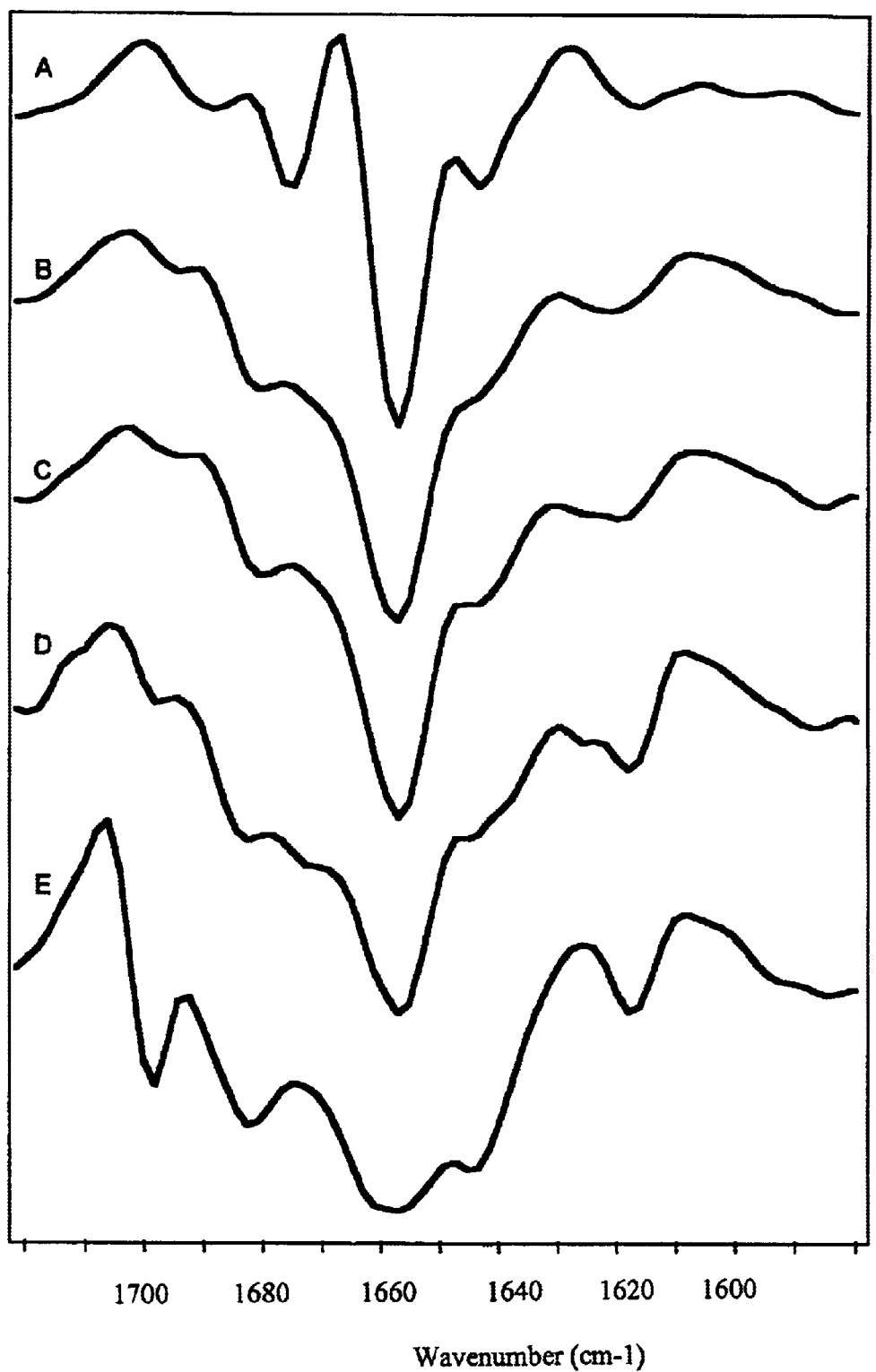
Figure 10:
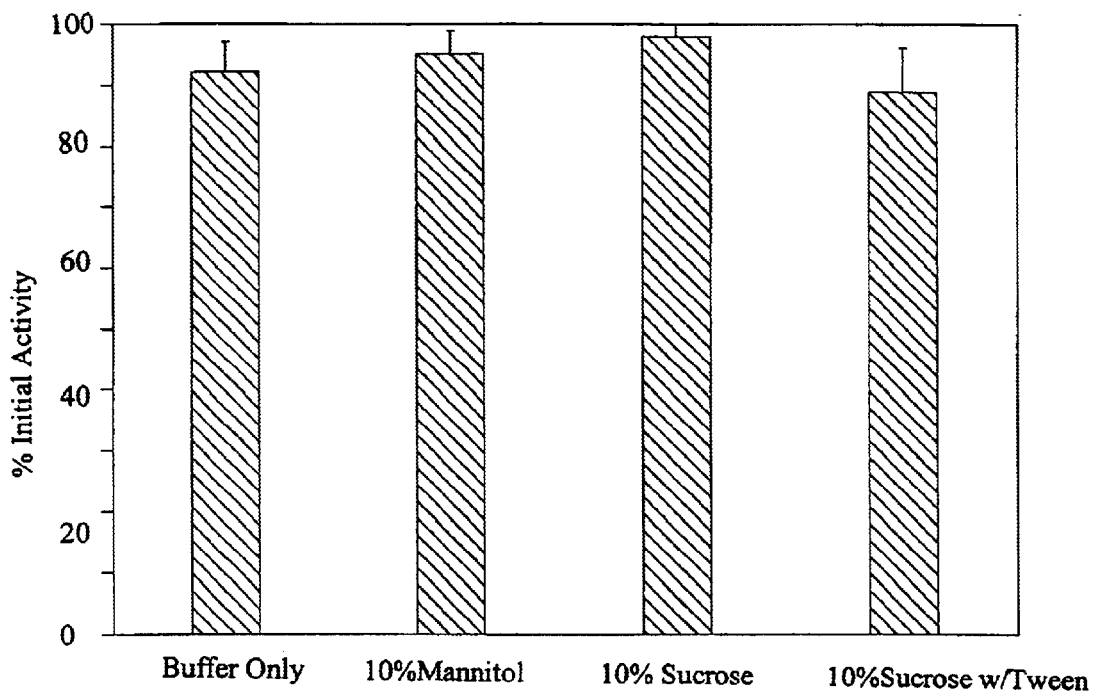

The restrictor may have a shaped or substantially flat end. The end of a restrictor may be mechanically shaped. For example, part of the material may be removed using an abrasive. Some suitable abrasives include diamond-embedded nickel alloy pads, of the kind used by marble sculptors made by 3M, for example. Very small (micron sized) diamond crystals abrade away the walls around each channel. The restrictor type shown in FIG. 3 after shaping with a diamond pad is shown in FIG. 4. Alternatively, fine frit silicon carbide "wet-dry" sandpaper can be used. The silicates in grout or tile can abrade and shape the restrictor. Diamonds are preferred.

Layers of the restrictor may also be etched away chemically. For example, selective layers of a glass restrictor may be etched with HF. One procedure that may be used is to force air in the tip slowly and dip the restrictor deeper and deeper into hydrofluoric acid (aq.). This will taper the end to a pencil-like tip point. Other suitable chemicals may be used. For example, if the restrictor is metal, an acid such as hydrochloric acid may be used to remove layers. Combinations of mechanical and chemical etching may be used.

The angle of the conical tip may be varied from very acute to very sharp (from about 5 degrees from the plane of the body of the restrictor to about 89 degrees from the plane of the body of the restrictor). The angle of the conical tip determines the volume in which the droplets will form, with a more acute angle increasing the volume at which the droplets will form. When the angle is more acute, the channel outlets appear as long ellipsoids, rather than round holes. Spraying over the area of a hemisphere (rather than in a single direction) allows droplets to be rapidly dispersed in the drying gas with less agglomeration.

The benefits of using a multichannel restrictor include increased throughput relative to a single channel restrictor and the ability to continue forming particles if some channels are blocked or clogged. The benefits of using an elongated exit for fluids include: 1) a more dispersed (axially) plume of aerosols which helps avoid problems of aggregation of particles after formation and 2) a better mixed fluid.

The multichannel restrictor may be used to form particles of various substances, including fluids; melts; solutions; supercritical fluids and solutions or suspensions of supercritical fluids and aqueous and/or organic solvents; emulsions; microemulsions; micelles; reverse micelles and other substances into aerosols containing fine particles of solids (amorphous or crystalline). These aerosols may be dried using the methods described herein, or other methods known to the art. The multichannel restrictor may also be used in fire extinguishers, where free radical scavengers can be used in combination with removal of heat to smother a fire. An aerosol cloud of very finely divided water droplets containing radical scavenger has higher surface areas and droplet suspension lifetime without sedimentation than larger water droplets prepared by conventional spray nozzles without $CD_2$.

EXAMPLES

Materials

Microcrystalline egg white lysozyme, crystallized (3×), dialyzed in water and lyophilized was purchased from Sigma Chemical Co. lot#53H7145. Lactate dehydrogenase was obtained as an ammonium salt suspension, purchased from Sigma Chemical Co. (isolated from rabbit muscle, $M_4$ isoenzyme lot#95H9550) and from Boehringer-Mannheim (isolated from porcine heart, $M_4$ isoenzyme, Batch #84895527). Sucrose and mannitol were purchased from Pfanstiehl Laboratories and used without further purification. Polyoxyethylene (20) sorbitan monolaurate (Tween 20) and buffer salts were purchased from Aldrich Chemical and used without further purification. Carbon Dioxide (SFE grade, siphon tank) was purchased from Scott Specialty Gases.

Methods

Preparation of the Enzymes. Lysozyme solutions were prepared by the addition of the solid, previously lyophilized, material to the desired formulation. Lysozyme is a fairly robust protein that is not significantly damaged upon lyophilization or conventional spray drying. The lyophilized powder was allowed to slowly diffuse into solution at a temperature between 2 and 8° C. The LDH ammonium sulfate suspensions were dialyzed against 100 mM potassium phosphate (pH 7.5) at a temperature between 2 and 8° C. for 12 to 24 hours. The resulting solution was then diluted to a concentration of 100 mg/mL of protein in water.

Nebulization and Bubble Drying System. The system used for supercritical $CO_2$-assisted nebulization is summarized here briefly (diagram in FIG.1). An aqueous stream and a stream of supercritical or near critical carbon dioxide (T>32° C., P=1500 psi) were each delivered at a constant flow rate of approximately 0.3 mL/min into each of two legs of a low dead volume mixing tee (Valco) using a HPLC solvent delivery pump (Waters model M-6000A) for the aqueous stream and a syringe pump (ISCO Model 260D, set to deliver at a constant pressure of 1500 psi) for the carbon dioxide. The two streams, initially at room temperature, were heated to just above 32° C., by a thermocouple-controlled cartridge heater attached to the mixing tee. The resultant emulsion that formed inside the mixing tee was allowed to expand out of the third orifice of the tee which was fitted with a 50 $\mu$m inner-diameter 5 cm long fused silica pressure restrictor (Alltech). The rapid decompression of the supercritical fluid as it exited the pressure restrictor, coupled with the explosive release of dissolved carbon dioxide from the aqueous solution caused the formation of very fine aqueous droplets containing some residual dissolved carbon dioxide. This aerosol was then directed into a custom-built drying chamber consisting of a 30 cm×2 cm borosilicate glass tube fitted with 4 gas inlet ports at the top of the tube and a powder filtration apparatus (stainless steel Millipore filter holder, 0.2 μm pore size cellulose acetate filter paper) followed by a cold trap and vacuum pump at the bottom of the tube. Heated dry nitrogen at a flow rate of approximately 15 L/min was added concurrently with the aerosol through the four gas inlet ports at the top of the drying tube. Additionally, the tube was heated externally with an infrared lamp to aid in the drying process and to keep water from condensing on the inner walls of the tube. The resultant temperature inside the drying chamber was maintained below 70° C. during nebulization, which was sufficient to cause rapid bubble drying.

Once the system was equilibrated by nebulizing and drying pure water for 10 to 15 minutes, an aqueous protein formulation (containing between 2 and 20% w/w total solids) was injected into the aqueous feed line via an HPLC-type injection port. This type of injection port allows for very small volume aliquots (between 0.5 and 5 mL) of the aqueous protein formulation to be nebulized, dried and collected, which is especially useful when working with limited quantities of protein. The design of this system allowed for the collection of the dried powder under a constant purge of warm dry nitrogen, which was continued after completion of the experiment to remove excess water vapor from the drying chamber. The filter paper apparatus was then isolated from the system and transferred to a dry nitrogen-purged glove bag, where the powder was transferred into 1.5 mL microcentrifuge tubes and capped and stored in desiccators over conc. sulfuric acid until analysis. In some experiments, the vacuum pump was used to draw the water vapor, carbon dioxide, and nitrogen through the filter at pressures slightly below atmospheric (630 mm Hg in Boulder, Colo. at its mile-high elevation). In other experiments the vacuum pump was eliminated and the drying was conducted at pressures slightly above ambient, with equivalent results (data not shown).

Static and Dynamic System pH Measurements

In order to simulate the conditions inside the low dead volume mixing tee in an observable static system, unbuffered and buffered solutions mixed with Fisher pH indicating solution were filled into a high pressure chamber equipped with sapphire windows, a pressure transducer, thermocouple relay-controlled heating cartridges and a magnetic stirring mechanism. The contents of the cell were equilibrated at 35° C., with stirring, and pressurized to 1500 psi with $CO_2$. In order to determine the degree of increased acidity due to pressurization of the aqueous formulations with carbon dioxide, a series of pH measurements was made on buffered and unbuffered solutions. In a second, more quantitative approach, buffered and unbuffered solutions were nebulized with the supercritical $CO_2$ system and collected as wet aerosols until the level of the aqueous solution in the collection vessel permitted a measurement by a pH probe.

Experimental Design

Samples for powder characterization were prepared with supercritical $CO_2$-assisted nebulization and bubble drying from the following aqueous lysozyme formulations: "buffer only" consisted of 4 mg/mL lysozyme and 100 mM potassium phosphate buffer (pH 7.0). "10% mannitol" consisted of 4 mg/mL lysozyme, 100 mM potassium phosphate buffer (pH 7.0) and 10% w/w mannitol. "10% sucrose" consisted of 4 mg/mL lysozyme, 100 mM potassium phosphate buffer (pH 7.0) and 10% w/w sucrose and "10% sucrose w/Tween" consisted of 4 mg/mL lysozyme, 100 mM potassium phosphate buffer (pH 7.0), 10% w/w sucrose and 0.01% w/w Tween 20 (polyoxyethylene (20) sorbitan monolaurate). Prior to nebulization, all formulations were filtered through 0.2 μm Nylon syringe filters to remove any particulates. Approximately 2 mL of each formulation was injected into the nebulization system for each run, except for the buffer only formulation, which was injected at 6 mL volume per run due to the low total solute content of this formulation (in an effort to collect enough powder per run for analysis). Each formulation was injected three times and each powder batch was collected separately to determine the run to run consistency of the system. Additionally, powders containing LDH were prepared from aqueous formulations consisting of 0.1 mg/mL LDH and 100 mM potassium phosphate (pH 7.5), and with the following excipients: 10% w/w mannitol; 10% w/w sucrose; and 10% w/w sucrose with 0.01% w/w Tween 20. These concentrations refer to percentages in the aqueous solution before bubble drying; the concentrations in the dried powders become proportionately larger as the water is removed.

Size Exclusion Chromatography

The presence of soluble aggregates was determined by size exclusion chromatography performed on a Dionex HPLC equipped with a model AD20 UV detector set to 280, a GP40 gradient fluid pump and a Spectra Physics autosampler. The stationary phase consisted of a 30 mm×7.8 mm (i.d.) TosoHaas TSK-Gel G3000$SW_{x1}$ column of 5 mm silica beads with a pore size of 250 Å. The isocratic mobile phase consisted of 100 mM potassium phosphate buffer (pH 7.0). Prior to injection, powder samples were rehydrated to the original, pre-dehydrated, total solids weight to total solution weight ratio with deionized water. The rehydrated samples were centrifuged and loaded into the autosampler in septa-capped HPLC vials. The flow rate was set to 0.5 mL/min, and approximately 10 mL of each sample was injected onto the column. Horseradish peroxidase, myoglobin, BSA, and ovalbumin were used as molecular weight standards. Each sample was injected three times and an average of each peak area was determined.

Scanning Electron Microscopy

Powders were examined using an ISI-SX-30 and a Jeol JSM-6400 scanning electron microscope (SEM) operating at an acceleration voltage of 30 kV. Samples were adhered to aluminum stubs using carbon tape and were gold sputter coated prior to analysis.

Thermal Analysis

Differential scanning calorimetry (DSC) was performed on a Perkin-Elmer DSC-7. Powders (5 to 10 mg) were loaded into anodized aluminum pans and hermetically sealed under nitrogen in a humidity controlled atmosphere (<2% relative humidity). Each sample was rapidly cooled to −20° C., held at −20° C. for 10 min and then heated to 200° C. at a heating rate of 10° C./min. $T_g$ is the glass transition temperature (glass→liquid). $T_m$ is the melting temperature of solid→liquid.

X-ray Powder Diffraction

Powder X-ray diffraction was carried out on a Sintag PADV system equipped with a $CuK_\alpha$ source (1=1.54056 Å) operating at a tube load of 40 kV and 25 mA. To determine the presence or absence of crystallinity in the powders prepared by supercritical $CO_2$-assisted nebulization and bubble drying, samples were scanned over a range of 2θ from 5° to 50° at a scan rate of 0.02°/minute.

Moisture Analysis

Karl Fisher titrations were performed on a Mettler Karl Fisher automatic titrator. Samples for analysis were prepared in a nitrogen purged glove box maintained below 1% relative humidity. Approximately 1 mL of anhydrous methanol or formamide was added to 25 mg of sample powder. The resulting suspension was sonicated for several minutes. 100 mL of the solution was injected into the coulometer and the moisture content of the powder was determined after subtraction of the background moisture content of the solvent in which the powders were suspended. Analysis of each powder sample was performed in triplicate.

Infrared Spectroscopy

Infrared spectra were obtained on a Bomem PROTA infrared spectrophotometer. Lyophilized powders (ca. 0.5 mg protein) were mixed with 300 mg anhydrous KBr and compressed into a pellet with a 13 mm evacuable die. The pellets were placed directly into the nitrogen purged sample chamber of the spectrophotometer. Aqueous solutions of native protein (20 mg/mL) were placed in a sample cell containing $CaF_2$ windows separated with a 6 mm Mylar spacer. An average of 128 scans was collected with 4 $cm^{-1}$ resolution in the 4000–900 $cm^{-1}$ range and Fourier transformed. For aqueous samples, the spectra of liquid water and water vapor were subtracted from the protein spectra of the protein solutions according to previously established criteria. (Dong, A. et al. (1990), "Protein secondary structures in water from second-derivative amide I infrared spectra," Biochem. 29:3303–3308; Dong, A. and Caughey, W. S. (1994), "Infrared methods for study of hemoglobin reactions and structures," Methods Enzymol. 232:139–175; Dong, A. et al. (1995), "Infrared Spectroscopic Studies of Lyophilization—and Temperature—Induced Protein Aggregation," J. Pharm. Sci. 84:415–424.) The second derivative for the Fourier transformed spectra was calculated and a Savitzky-Golay smoothing of the data was applied with a seven-point convolution window to reduce possible white noise.

Lysozyme Enzymatic Activity Assay

A bacterial suspension of *Micrococcus lysodeikticus* (Sigma lot #38H8619) at a concentration of 0.25 mg/mL in 67 mM phosphate buffer (pH 6.6) was prepared. The lysozyme solutions were diluted to 4 mg/mL enzyme with the phosphate buffer. The reaction mixture consisted of 2.5 mL of the cell suspension and 0.1 mL of the enzyme dilution. The enzymatic activity was proportional to the rate of the decrease in turbidity of the cell suspension, which was measured spectrophotometrically as a linear decrease in absorbance at 450 nm for 2 min.

LDH Enzymatic Activity Assay

LDH activity was measured at 25° C. in a 2 mL reaction mixture consisting of 25 mM tris(hydroxymethyl) aminomethane/tris(hydroxymethyl) aminomethane hydrochloride (Tris/Tris HCl, pH 7.5), 100 mM KCl, 2 mM pyruvate (Sigma, lot #126H10981), and 0.15 mM NADH (Sigma lot #027H78191). The LDH preparation (10 mL) was added to the reaction mixture, the cuvette was inverted 3× and the absorbance decrease at 340 nm was monitored with a spectrophotometer. Activity was measured immediately prior to supercritical $CO_2$-assisted nebulization and immediately after rehydration of the dried powders and reported as a percentage of initial activity. Note in FIG. 11 the LDH activity is greater than 100% of the activity of the initial aqueous solution for certain compositions.

Static and Dynamic pH Measurements with and without Buffers

The question of whether the acidification occurring when $CO_2$ is dissolved in water could be avoided by the use of buffers was studied. The solubility of $CO_2$ (approximately 2 mole % at 35° C.) in water at 1500 psi causes an increase in acidity in unbuffered solutions. In the absence of buffers, an acidic environment could potentially denature proteins. For these reasons, a static system was used to simulate the conditions within the mixing tee in order to observe the extent of the increase in acidity of an aqueous solution without buffering. pH sensitive indicator dyes were added to the aqueous solution prior to pressurization with carbon dioxide to qualitatively monitor the change in acidity. As expected, the pH rapidly decreased below the indicator range (pH<4) immediately upon pressurization. The capability to neutralize this effect was estimated with this static system for the following buffer salts: monobasic/dibasic potassium phosphate (pH 7), Tris/Tris HCl (pH 7.2), citric acid/sodium citrate (pH 5.5), and acetic acid/sodium acetate (pH 5). The buffering capacity for all solutions tested, measured as the ability of the buffer system to forestall the color change of the indicator dye, leveled off at approximately 100 mM concentration (data not shown). To further quantitate these observations, the same buffers used in the static system were nebulized with the supercritical $CO_2$ system and collected as wet aerosols. The pH of each solution had to be measured immediately after collection as the value continued to increase due to carbon dioxide effervescence. The results of this experiment are presented in FIG. 5 and are consistent with the static observations that 100 mM buffer will adequately neutralize the effects of dissolved $CO_2$ and avoid damage to proteins that are damaged by acidification.

Fine Powder Characterization

In order to determine the surface characteristics of molecules produced by the method of the current invention, fine powders of albuterol sulfate, tobramycin sulfate, cromolyn sodium, rhDNase, lactose, and sodium chloride were prepared using the method outlined above. Conditions for droplet formation were $CO_2$ pressure: 1500 psi, 0.3 mL/min flow rates, $CO_2$ and $H_2O$ concentrations were about 10% (wt/vol), tube inlet ~70° C., tube outlet ~50° C., 50 mm, 5 cm fused silica restrictor, 0.2 mm cellulose acetate filter paper.

FIG. 6 shows electron micrographs of representative dry powders prepared using the method of this invention. FIG. 6A is a transmission electron microscopy (TEM) image of dried sodium chloride particles prepared from the method of the invention using a 20% aqueous sodium chloride sample. FIG. 6B is a scanning electron microscopy (SEM) image of the same sodium chloride solution after drying by the method of this invention. FIG. 6C is a TEM image of mannitol. FIGS. 6D and 6E show tobramycin sulfate particles (6D) and 1% tobramycin sulfate in lactose particles (6E) prepared by the method of this invention on a 10% (total solute mass/volume) aqueous solution. FIG. 6F is an image of albuterol sulfate particles produced by the method of this invention. FIG. 6G is an image of cromolyn sodium particles produced by the method of the invention.

Dry powders were initially prepared by $CO_2$-assisted nebulization and bubble drying from the aqueous lysozyme formulations described in Materials and Methods. Visually, the collected samples were all very fine white powders with very little run to run variability in the quality of the powders. All powders were hygroscopic in moist air, but were free flowing and easily handled in a low-moisture environment. Electron micrographs of representative dry powder protein formulation are shown in FIG. 7. "Buffer only" powder (A) 10% mannitol (B), 10% sucrose (C), and 10% sucrose with 0.01% Tween 20 (D). Note that when Tween is used, (see FIG. 6D), a powder with less agglomerated particles and more distinctly spherical, individual particles is formed. This may be a direct or indirect effect from the addition of surfactant Tween 20. Without wishing to be bound by any particular theory, it is believed that the detergent aids in dehydration during processing. All powders produced had significant portion of particles well within the 1 to 3 mm diameter inhalable size range. The morphology of the powders prepared from the buffer only formulation and the formulation containing 10% mannitol appear to be significantly less spherical and smooth than the powders prepared from the formulations containing sucrose. The addition of Tween 20 to the sucrose solution had an effect to even further smooth out the surface of the dried particles. This has been observed by other researchers for particles that were conventionally spray-dried and it is postulated that the addition of a surface active agent to the aqueous formulation has an effect to reduce surface turbulence during the dehydration process.

The micrograph of the 10% mannitol formulation (FIG. 7B), indicates a more crystalline material as seen by the multi-faceted particles.

Moisture Analysis

Karl Fischer moisture analysis on lysozyme powders dried by the method of the invention also indicated low moisture contents: the moisture content of samples of 4 mg/mL lysozyme with 10% (percentage in initial aqueous solution) mannitol was 0.6±0.05%; the moisture content of powders of 4 mg/mL lysozyme with 10% sucrose was 1.18±0.02% and the moisture content of powders of 4 mg/mL lysozyme with 10% sucrose and 0.01% Tween was 1.25±0.07%.

The Karl Fisher titration results performed on each LDH powder prepared by supercritical $CO_2$-assisted nebulization and bubble drying indicate that quite low moisture contents are attainable for this new process: the moisture content of the powder prepared from the buffer only aqueous formulation was 0.83+0.06% w/w, 1.3+0.01%, from the 10% mannitol formulation, 1.4+0.08% form the 10% sucrose formulation, and 3.25+0.03% from the formulation containing 10% sucrose and 0.01% Tween 20. The collected sucrose powders were very hygroscopic, and had to be handled in a gloved bag under an atmosphere of dry nitrogen. Other sugar powders, e.g., trehalose, are less hygroscopic.

XRD and DSC

Because the crystallization of excipients can have dramatic effects on the solubility and stability of solid pharmaceutical formulations, the ability to form crystalline and/or amorphous powders with supercritical $CO_2$ assisted nebulization was investigated. The strong tendency of mannitol to crystallize during freeze-drying and to form crystalline powders upon spray drying is well known. Therefore, mannitol was chosen as an excipient to determine the capability of the nebulization system to form crystalline powders, although this excipient was not expected to stabilize the model proteins to a significant degree. While crystallinity is a desired attribute for excipients used as bulking agents for solid pharmaceuticals, excipients that tend to crystallize during processing offer very little protection to labile protein drugs during dehydration and subsequent storage in the dried state. The powder diffraction data for a lysozyme sample prepared from the 10% mannitol formulation appears in FIG. 8 for samples prepared by supercritical $CO_2$-assisted nebulization. Aqueous formulations contained 4 mg/mL lysozyme, 100 mM phosphate buffer at pH 7.0 and were nebulized together with 10% mannitol (A) or 10% sucrose (B). Final approximate solid weight percentage in the bubble dried powders: 4% protein, 16% buffer and 80% sugar. The diffraction data of the powder prepared from the 10% mannitol solution indicates good crystallinity within the sample and appears to be a mixture of the a and b polymorphs of mannitol. This diffraction pattern is consistent with the powder diffraction pattern obtained for pure D-mannitol as received from the vendor (not shown).

DSCs for mannitol as received, mannitol spray dried with lysozyme, sucrose spray dried with lysozyme and sucrose and lysozyme are not shown. The DSC of a sample of mannitol as received showed a peak from 157.25 to 177.56° C.; onset 156.10° C. $T_m$ was 159° C.; 300.47 J/g. PSC of a sample of mannitol spray dried with 4 mg/mL lysozyme showed a peak onset from 77.63 to 146.48° C. $T_m$=154.7° C.; 134 J/g uncorrected. DSC of sample of sucrose with 4 mg/mL lysozyme showed $T_g$ from 21.93 to 47.12° C. with onset 40.25° C. $T_g$=43.05° C. and 1.51 J/g deg uncorrected. DSC of sucrose with Tween and 4 mg mL lysozyme showed $T_g$ from 28.57 to 56.99° C.; onset 45.36° C.; 1.00 J/g deg; $T_g$=50.95° C.

The X-ray powder diffraction data of the sucrose formulations (FIG. 6B), indicate a more amorphous nature confirmed by the glass transition observed in the DSC thermograms. The ability to form amorphous glassy powders below the glass transition temperature is an important capability of the disclosed system, as significant evidence has been found recently linking protein stabilization with vitrification (glass formation) (Crowe, J. H. et al. (1998), "The Role of Vitrification in Anhydrobiosis," Annu. Rev. Physiol. 60:73). Differential scanning calorimetry of the sample indicated the presence of an endothermic event at 154.7° C., which is consistent with the melting temperature of crystalline D-mannitol (169° C.). The depressed $T_m$ is probably due to the presence of water (approximately 1% as measured by Karl Fisher titration) in the powder.

Characterization of Rehydrated Solutions

Powders collected on the filter paper were transferred to small inert tubes and rehydrated with distilled, deionized water to the original wt/wt% (total solute mass/total solution mass). Activity assay of the rehydrated protein solutions compared to the original solutions indicated greater than 90% activity retention (or recovery) for all solutions sprayed. HPLC (size exclusion Tosohaas column TSK3000SW$_{XL}$, 100 mM KPO$_4$ pH=7.0 elution buffer) indicated that the ratio of monomeric protein to dimeric aggregates remained constant after drying and rehydration (aggregate formation to produce dimers, trimers and eventually insoluble aggregates is a common protein degradation pathway). HPLC data are not shown. The aggregate:monomer ratio was calculated to be approximately 0.21%±0.02% for the initial lysozyme formulations and for all rehydrated powders.

Researchers believe that one important method for stabilizing a protein in the solid state is to provide the protein with a matrix in which native protein structural conformation can be, at least somewhat, preserved upon dehydration (Chang, B. S. et al. (1996), "Physical Factors Affecting the Storage Stability of Freeze-Dried Interleukin-1 Receptor Antagonist: Glass Transition and Protein Conformation," Arch. Biochem. Biophys. 331:249; Allison, D. S. et al. (1998), "Effects of Drying Methods and Additives on Structure and Function of Actin: Mechanisms of Dehydration-Induced Damage and Its Inhibition," Arch. Biochem. Biophys. 358:171). Dehydration-induced structural transitions have been shown to be inhibited by the addition of certain stabilizers, such as sucrose, to the protein solution before processing (Prestrelski, S. J. et al. (1993), "Dehydration-induced Conformational Transitions in Proteins and Their Inhibition by Stabilizers," Biophys. J. 65:661). Second derivative Fourier-transformed infrared spectroscopy (Carpenter, J. F. et al. (1998), "Application of Infrared Spectroscopy to Development of Stable Lyophilized Protein Formulations," Eur. J. Pharm. Biopharm. 45:231) in the amide I region (1600–1700 $cm^{-1}$) was used to probe the conformational structure of the dried lysozyme powders. Representative results are shown in FIG. 9. Samples of (A) lysozyme in the native aqueous state; (B) lysozyme containing 10% sucrose and 0.01% Tween 20; (C) lysozyme with 10% sucrose; (D) lysozyme with 10% mannitol; and (E) lysozyme with buffer only were dried at 70° C. The amide I region shows characteristic C=0 stretching frequencies for different types of secondary structures. Interestingly, while enzymatic activity was almost fully retained upon rehydration of all powders, the dried lysozyme powders showed markedly different protein conformations in each formulation. When compared to the native lysozyme liquid infrared spectrum, the formulation without any excipient showed the largest deviation from native conformation, the 10% mannitol formulation showed somewhat less deviation from the buffer only formulation, while the 10% sucrose formulation showed even less deviation from the native structure. The 10% sucrose plus Tween 20 formulation showed the most native-like structure of all the powders. These results indicate that lysozyme was not irreversibly damaged by our nebulization and drying process. The protein structure, however, showed significant deviation from the native conformation in the dry powders. The recovery of activity seems to indicate the ability of lysozyme to recover its native conformation upon rehydration. The conformational transitions observed in the drying process can be inhibited by the addition of disaccharide stabilizers such as sucrose.

Without wishing to be bound by theory, it is believed that sugars hydrogen bond to the protein in place of water molecules, thereby reducing conformational changes in the protein structure upon dehydration. It is believed that surfactants reduce the amount of stress at the air-water interface that the protein is subjected to by competing for the available air-water interface regions with the protein. Surfactants added to the protein formulation are believed to prevent aggregation of the protein molecules.

Lysozyme Activity Assay

Enzymatic activity of the lysozyme powders rehydrated to their original total solute % (w/w) was measured immediately after rehydration. These results (FIG.10) are reported as a percentage of the initial activity that was independently measured immediately before supercritical $CO_2$-assisted nebulization and bubble drying. Results are an average of at least three measurements, and error bars represent one standard deviation. Analysis of lysozyme powders indicated greater than 90% recovery of initial activity for all formulations. The observed recovery of activity is an indication of the reversibility of the structural change in this protein upon dehydration and rehydration. Thus, although lysozyme is severely unfolded upon dehydration during supercritical $CO_2$-assisted nebulization in the absence of amorphous stabilizers, it can readily refold upon rehydration, and, thereby, recover much of its original biological activity.

LDH Activity Assay

In order to further examine the nebulization process, studies were performed using a significantly more labile enzyme, lactate dehydrogenase (LDH, Sigma, L-5762). Data are shown in FIGS. 10 and 11. LDH is known to be damaged by conventional drying processes (Adler, M. and Lee, G. (1999), "Stability and Surface Activity of Lactate Dehydrogenase in Spray-Dried Trehalose," J. Pharm. Sci. 88:199). LDH was dialyzed against the 100 mM potassium phosphate buffered to pH=7.5 at room temperature for at least 12 hours. Protein concentration was kept constant at 100 μg/mL. The LDH formulations were dehydrated using the same conditions used for bubble drying the lysozyme formulations. The powders prepared from the LDH solutions appeared visually identical to the powders containing lysozyme (data not shown).

Dry powders comprising LDH were produced from formulations containing 10% mannitol, 10% sucrose and 10% sucrose plus 0.01% Tween 20, along with LDH (100 μg/mL) and potassium phosphate buffer (100 mM, pH=7.5). The activity of the rehydrated powders was compared to the original formulations before nebulization and drying.

Four different formulations were prepared:

Buffer only

- 0.1 mg/mL LDH
- 100 mM $KPO_4$ (pH 7.5)

10% Mannitol

- 0.1 mg/mL LDH
- 100 mM $KPO_4$ (pH 7.5)
- 100 mg/mL mannitol

10% Sucrose

- 0.1 mg/mL LDH
- 100 MM $KPO_4$ (pH 7.5)

100 mg/mL sucrose
10% Sucrose with Tween
0.1 mg/mL LDH
100 mM $KPO_4$ (pH 7.5)
100 mg/mL sucrose
0.1 mg/mL Tween 20

Figure 11:
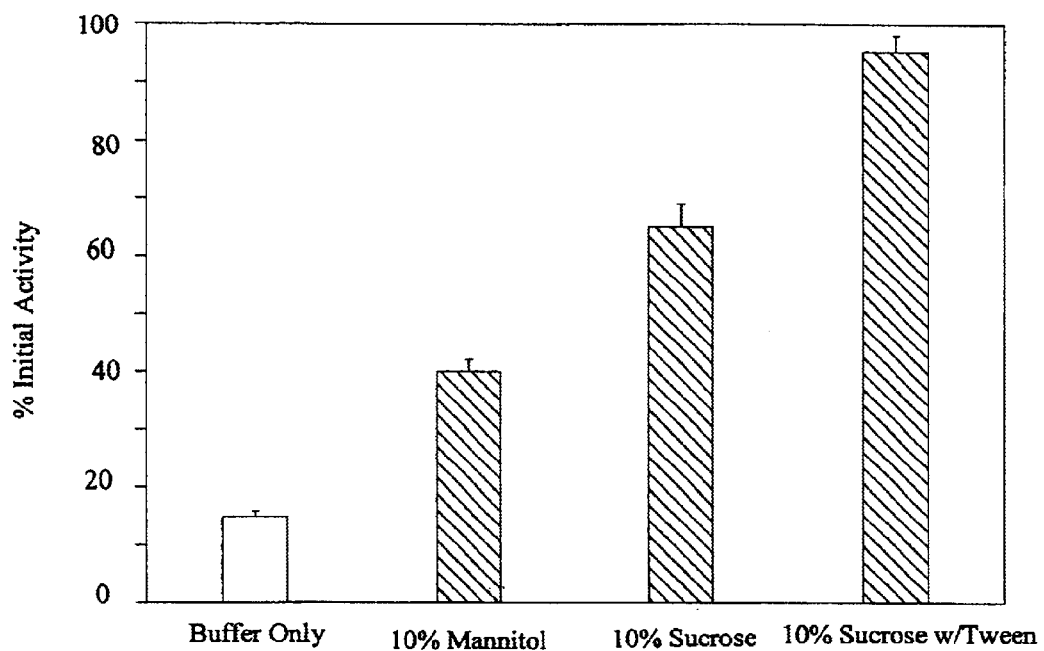
Figure 12:
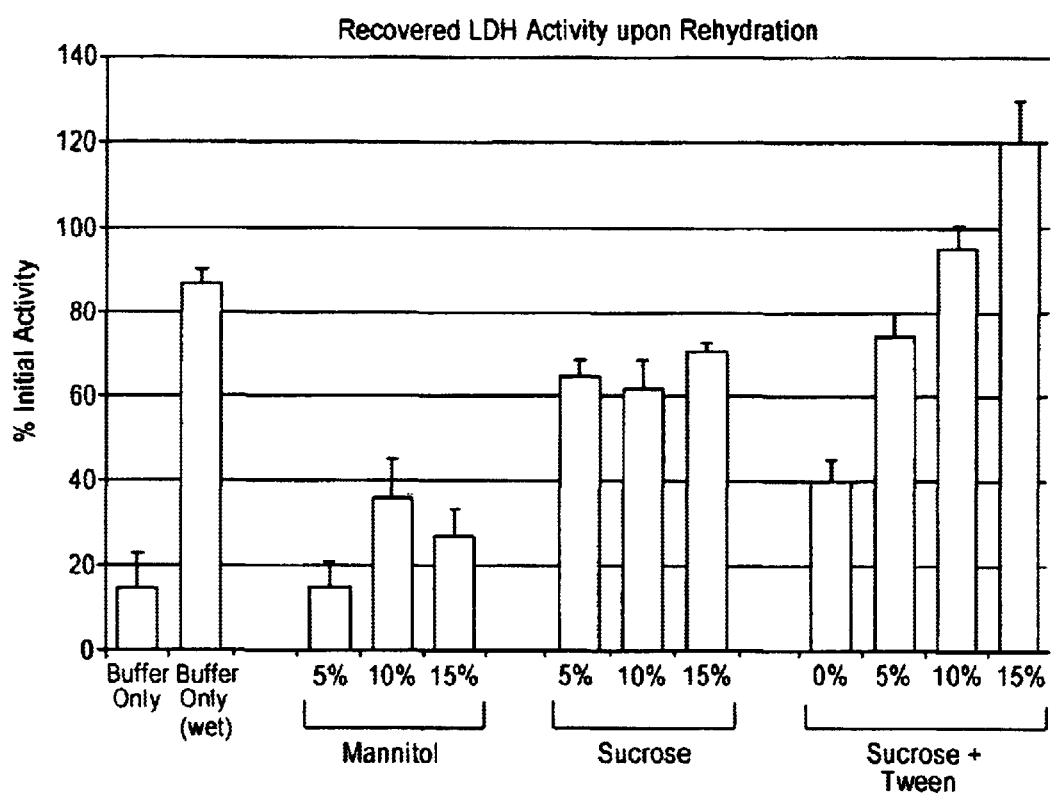

The LDH catalytic activity recovery for these formulations is shown in FIG.11. LDH, nebulized and dehydrated without any added excipients, recovers only 15% of its original activity after rehydration. Interestingly, the same solution collected as a wet aerosol retained 87% of its original enzymatic activity. This result indicates that most of the damage experienced by the protein occurs in the drying process after the aqueous solution/$CO_2$ emulsion is ejected from the restrictor tip. In other words, $CO_2$-assisted nebulization is not as harsh as the drying of micro-droplets and micro-bubbles in nitrogen at 70° C. The irrecoverable damage experienced during the dehydration process was partially prevented by the addition of mannitol, and to a greater degree with sucrose. Activity loss was almost completely prevented by the addition of sucrose and Tween 20. These results are as expected from the structural analysis of the lysozyme formulations as LDH, a more labile, tetrameric enzyme is not expected to have the same ability to refold upon rehydration as lysozyme. As a result, activity was better preserved when LDH was dried in the presence of sucrose as it is most likely that the protein's structure was preserved.

FIG. 12 compares recovery of activity upon rehydration for varying percentages of mannitol, sucrose and (sucrose+Tween (0.01%)). Note that the percent recovery of initial activity shows the most dramatic change with concentration of sugar when Tween is used in the formulation.

In general these results indicate that the damage experienced by LDH during the supercritical $CO_2$-assisted nebulization and bubble drying can be inhibited by the addition of a sugar stabilizer and even further with the combination of 10% sucrose and 0.01% surfactant, Tween 20. The formulated protein appears to be successfully protected throughout the dehydration process experienced during supercritical $CO_2$-assisted nebulization and bubble drying.

The mechanism(s) by which Tween 20 increased protection in the presence of sucrose during supercritical $CO_2$-assisted nebulization and bubble drying is uncertain at this point. Tween 20 may protect the protein by saturating surface sites at the air-liquid interface thereby preventing surface denaturation. The air-liquid interface is expected to be significant for this process due to the high surface area micro-droplets produced by supercritical $CO_2$-assisted nebulization. Additionally, the surfactant may offer protection by saturating hydrophobic sites on the surface of the protein, which are potential sites for aggregation. Furthermore the surfactant may foster protein refolding during rehydration. Whether Tween 20 is protecting LDH by one or more of these mechanisms during nebulization and bubble drying is undetermined at this point. This protein protection effect, combined with the improved particle separation and smoothness noted in sucrose formulations containing Tween 20, clearly document the potential benefits of including this surfactant in formulations dried by supercritical $CO_2$-assisted nebulization and bubble drying. It was also noted in some C., experiments that the enzymatic activity of aqueous LDH after compression with $CO_2$, decompression, and bubble drying was apparently greater, as indicated by enzymatic analysis, than the initial aqueous solution before compression at 2000 psi (see FIG.12). It has been demonstrated by St. John, Carpenter and Randolph that protein refolding is facilitated by pressurizing aqueous solutions at 20,000 psi ("High Pressure Fosters Protein Refolding from Aggregates at High Concentrations," Proc. Natl. Acad. Sci. 96:13029, 1999). At this time, the cause of the improved activity is not known. Although Applicant does not wish to be bound by theory, treating aqueous solutions by compression with $CO_2$ with a surfactant may produce apparent improved activity due to the surfactant, the moderate pressure, the presence of carbon dioxide, or sugar, or by other mechanisms.

Although the description above contains many specificities, these should not be construed as limiting the scope of the invention, but as merely providing illustrations of some of the presently-preferred embodiments of this invention. For example, many fine dry powders of many different substances can be used in the methods of the invention; other supercritical or near-critical fluids may be used than specifically exemplified; and additives other than those specifically exemplified may be used. The scope of the invention should be determined by the appended claims and their legal equivalents rather than by the examples given.

Each reference cited in the present disclosure is incorporated by reference herein to the extent not inconsistent with the disclosure herein.

We claim:

1. A method of forming fine dry particles, wherein the particles comprise substances which are either soluble in supercritical fluid, near critical fluid, or mixtures thereof, or substances which are soluble or suspendable in aqueous solutions, which method comprises:

(a) forming a composition comprising one or more substances and a supercritical or near critical fluid;

(b) reducing the pressure on said composition, whereby droplets are formed;

(c) passing said droplets through a flow of drying gas which is not the same substance as the supercritical or near critical fluid, said drying gas heated from above ambient temperature to about 100° C.

2. The method of claim 1, wherein the temperature of said drying gas at the point where said droplets are initially passed through said gas is below about 100° C.

3. The method of claim 1, wherein said one or more substances of step (a) is soluble in said supercritical or near critical fluid.

4. The method of claim 1, wherein said composition of step (a) also comprises an aqueous solvent.

5. The method of claim 4, wherein said one or more substances of step (a) is soluble in said aqueous solvent.

6. The method of claim 1, wherein said composition of step (a) also comprises one or more additives selected from the group consisting of: excipients, stabilizers, bulking agents and surfactants.

7. The method of claim 6, wherein said one or more additives comprise less than about 99.9% of the weight of the dry particles.

8. The method of claim 1, wherein said composition of step (a) also comprises a pH buffering substance.

9. The method of claim 1, wherein said supercritical or near critical fluid is carbon dioxide.

10. The method of claim 1, wherein said drying gas is nitrogen.

11. The method of claim 1, wherein said flow of drying gas of step (c) is contained within a drying chamber.

12. The method of claim 1, wherein said one or more substances of step (a) comprise a physiologically active composition selected from the group consisting of surfactants, insulin, amino acids, enzymes, analgesics, anti-cancer agents, antimicrobial agents, viruses, antiviral agents, antifungal pharmaceuticals, antibiotics, nucleotides, DNAs, antisense cDNAs, RNAs, peptides, proteins, immune suppressants, thrombolytics, anticoagulants, central nervous system stimulants, decongestants, diuretic vasodialators, antipsychotics, neurotransmitters, sedatives, hormones, anesthetics, anti-inflammatories, antioxidants, antihistamines, vitamins, minerals and other physiologically active materials known to the art.

13. The method of claim 1, further comprising:
(d) collecting said fine dry particles.

14. A method of forming fine dry particles comprising:
(a) mixing an aqueous solution containing one or more substances of interest and a supercritical or near supercritical fluid, forming a composition;
(b) reducing the pressure on said composition, whereby droplets are formed;
(c) passing said droplets through a flow of drying gas which is not the same substance as the supercritical or near critical fluid, said drying gas heated from above ambient temperature to about 100° C.

15. The method of claim 14, wherein the temperature of said drying gas of step (c) at the point where said droplets are initially passed through said drying gas is below about 100° C.

16. The method of claim 14, wherein said composition of step (a) also comprises one or more additives selected from the group consisting of: excipients, stabilizers, bulking agents and surfactants.

17. The method of claim 16, wherein said one or more additives comprise less than about 99.9% of the weight of the dry particles.

18. The method of claim 16, wherein if present, surfactants are present at a concentration of between about 0.001 to 0.5 wt %; and if present, stabilizers are present at a concentration of between about 0.05 to 25 wt %.

19. The method of claim 14, wherein the mixing is performed in a low dead volume tee.

20. The method of claim 14, wherein said one or more substances of step (a) comprise a physiologically active composition selected from the group consisting of surfactants, insulin, amino acids, enzymes, analgesics, anti-cancer agents, antimicrobial agents, viruses, antiviral agents, antifungal pharmaceuticals, antibiotics, nucleotides, DNAs, antisense cDNAs, RNAs, peptides, proteins, immune suppressants, thrombolytics, anticoagulants, central nervous system stimulants, decongestants, diuretic vasodialators, antipsychotics, neurotransmitters, sedatives, hormones, anesthetics, anti-inflammatories, antioxidants, antihistamines, vitamins, minerals and other physiologically active materials known to the art.

21. The method of claim 14, wherein said flow of drying gas of step (c) is contained within a drying chamber.

22. A method of forming fine dry particles comprising:
(a) equilibrating an aqueous solution of a substance of interest with a supercritical or near supercritical fluid, forming a composition;
(b) reducing the pressure on said composition, whereby droplets are formed;
(c) passing said droplets through a flow of drying gas which is not the same substance as the supercritical or near critical fluid, said drying gas heated from above ambient temperature to about 100° C.

23. The method of claim 22, wherein the temperature of said drying gas of step (c) at the point where said droplets are initially passed through said drying gas is below about 100° C.

24. The method of claim 22, wherein said composition of step (a) also comprises one or more additives selected from the group consisting of: excipients, stabilizers, bulking agents and surfactants.

25. The method of claim 24, wherein saidone or more additives comprise less than about 99.9% of the weight of the dry particles.

26. The method of claim 24, wherein if present, surfactants are present at a concentration of between about 0.001 to 0.5 wt %; and if present, stabilizers are present at a concentration of between about 0.05 to 25 wt %.

27. The method of claim 22, wherein said substance of step (a) is a physiologically active composition selected from the group consisting of surfactants, insulin, amino acids, enzymes, analgesics, anti-cancer agents, antimicrobial agents, viruses, antiviral agents, antifungal pharmaceuticals, antibiotics, nucleotides, DNAs, antisense cDNAs, RNAs, peptides, proteins, immune suppressants, thrombolytics, anticoagulants, central nervous system stimulants, decongestants, diuretic vasodialators, antipsychotics, neurotransmitters, sedatives, hormones, anesthetics, anti-inflammatories, antioxidants, antihistamines, vitamins, minerals and other physiologically active materials known to the art.

28. The method of claim 22, wherein said flow of drying gas of step (c) is contained within a drying chamber.

29. A device for forming fine dry particles, wherein the particles comprise a substance or substances which are either soluble in supercritical fluid, near critical fluid, or mixtures thereof, or substance or substances which are soluble or suspendable in aqueous solutions, consisting essentially of:
(a) a first pressurized chamber containing a first nongaseous supercritical or near critical fluid;
(b) a second chamber containing the solution or suspension of the substance or substances in a second non-gaseous fluid;
(c) a mixing chamber for mixing the solution or suspension of step (b) and first fluid connected to the first and second chambers by conduits;
(d) first flow control means connected to the conduit between the first chamber and the mixing chamber for passing the first fluid into said mixing chamber;
(e) second flow control means connected to the conduit between the second chamber and the mixing chamber for passing the second fluid into said mixing chamber;
(f) a restrictor connected to said mixing chamber for conducting the composition out of the mixing chamber into an expansion region having a pressure below that of the supercritical or near critical fluid where a dispersion of fine particles of said substance or substances is formed;
(g) a drying chamber connected to the restrictor;
(h) a source of gas which is not the same substance as the supercritical or near critical fluid, said source of gas connected to the drying chamber at one or more inlets;
(i) means for collecting particles after they pass through the drying chamber.

30. The device of claim 29, wherein said mixing chamber of step (c) is a low dead volume chamber.

31. The device of claim 29, wherein said first fluid is supercritical carbon dioxide.

32. The device of claim 29, wherein the first fluid of step (a) is a near-critical fluid.

33. The device of claim 29, wherein the second fluid of step (b) is aqueous.

34. The device of claim 29 wherein said substance or substances is a physiologically active composition selected from the group consisting of surfactants, insulin, amino acids, enzymes, analgesics, anti-cancer agents, antimicrobial agents, viruses, antiviral agents, antifungal pharmaceuticals, antibiotics, nucleotides, DNAs, antisense cDNAs, RNAs, peptides, proteins, immune suppressants, thrombolytics, anticoagulants, central nervous system stimulants, decongestants, diuretic vasodialators, antipsychotics, neurotransmitters, sedatives, hormones, anesthetics, anti-inflammatories, antioxidants, antihistamines, vitamins, minerals and other physiologically active materials known to the art.

35. A multichannel flow/pressure restrictor for the formation of particles of a substance from a composition comprising a supercritical or near critical fluid, the substance, and optionally an aqueous or organic solvent or combination of solvents, comprising:

(a) an inlet end for the introduction of the composition;

(b) an outlet end having plurality of openings; and (c) independent substantially parallel non-concentric path channels.

36. The multichannel restrictor of claim 35, wherein the outlet end is conically-shaped.

37. The multichannel restrictor of claim 35 wherein the channels consist of a honeycomb of ceramic channels with inner diameters of about 40–50 μm.

38. The multichannel restrictor of claim 35 wherein the restrictor is epoxied to a mixing tee.

39. A method of making the multichannel restrictor of claim 36 comprising mechanically or chemically shaping the outlet end.

40. The method of claim 39, wherein the mechanical shaping comprises applying stroking pressure to the outlet end with an abrasive.

41. The method of claim 39, wherein the chemical shaping comprises etching the outlet end in acid.

42. A method of preparing fine dry particles of lactate dehydrogenase (LDH) having improved activity upon rehydration than undried aqueous solutions of LDH comprising:

(a) forming a composition comprising less than 1 mg/ml LDH; greater than 5 wt % sugar; less than 0.5 wt % surfactant; water; buffer and a supercritical or near critical fluid where the percentages of sugar and surfactant are as present in the aqueous solution before drying;

(b) reducing the pressure on said composition, whereby droplets are formed;

(c) passing said droplets through a flow of gas which is not the same substance as the supercritical or near critical fluid, said drying gas heated to about 70° C.

43. A method of preparing fine dry particles of one or more biologically active substances having improved activity upon rehydration than undried aque